United States Patent [19]

Bristow et al.

[11] 4,120,960

[45] Oct. 17, 1978

[54] THERAPEUTIC AGENTS

[75] Inventors: Norman W. Bristow, Wollaton; Peter E. Macey, Nottingham; Kenneth J. Nichol, West Bridgford; Malcolm F. Sim, Woodborough, all of England

[73] Assignee: The Boots Company Limited, England

[21] Appl. No.: 820,907

[22] Filed: Aug. 1, 1977

Related U.S. Application Data

[63] Continuation-in-part of Ser. No. 519,541, Oct. 31, 1974, abandoned, which is a continuation-in-part of Ser. No. 412,354, Nov. 2, 1973, abandoned.

[30] Foreign Application Priority Data

Oct. 31, 1973 [GB] United Kingdom ............... 50623/73
Apr. 26, 1974 [DK] Denmark ............................ 2297/74

[51] Int. Cl.$^2$ ................. C07D 237/32; A61K 31/50; C07D 417/04
[52] U.S. Cl. .................................... 424/250; 424/246; 424/248.56; 544/51; 544/52; 544/58; 544/62; 544/105; 544/116; 544/237; 544/235; 260/154; 260/155; 260/157; 260/165; 260/152; 260/158; 260/162; 544/353; 544/283
[58] Field of Search .................... 260/250 P; 424/250

[56] References Cited

U.S. PATENT DOCUMENTS

| | | | |
|---|---|---|---|
| 3,497,512 | 2/1970 | Hofer et al. | 260/250 P |
| 3,833,579 | 9/1974 | Inoue et al. | 260/250 P |
| 3,870,792 | 3/1975 | Inoue et al. | 260/250 P |
| 3,963,716 | 6/1976 | Inoue et al. | 260/250 P |

OTHER PUBLICATIONS

Rowe et al.; J. Chem. Soc. (London) pp. 461–468 (1947).
Rowe et al.; J. Chem. Soc. (London) pp. 829–833 (1947).
Puodzuinas et al.; Chem. Abs. vol. 79: 137066b (1973).
Jaecklin et al.; Chem. Abs. vol. 76: 85263e (1972).
Simpson; *The Chemistry of Heterocyclic Compounds* Chap. XIV, pp. 106–118 (1953).
Foldeak et al.; Chem. Abs. vol. 73: 77173y (1970).

*Primary Examiner*—Donald G. Daus
*Assistant Examiner*—Mary C. Vaughn
*Attorney, Agent, or Firm*—Gordon W. Hueschen

[57] ABSTRACT

Therapeutic activity, and in particular the ability to induce diuresis or saluresis, has been discovered in 4-hydroxy- or 4-mercapto-2-aryl-1,2-dihydrophthalazine-1-acetic acids, the tautomers of these namely 4-oxo or thio-2-aryl-1,2-tetrahydrophthalazine-1-acetic acids, and in the ester and alcohol derivatives of the acids, and in the acyl derivatives of the 4-hydroxy or mercapto compounds and in the 3-alkyl derivatives of the 4-oxo or thio compounds. Therapeutic compositions and methods using the compounds are described, as also are novel compounds.

29 Claims, No Drawings

THERAPEUTIC AGENTS

This application is a continuation in part of our application Ser. No. 519,541 filed Oct. 31, 1974, now abandoned which was a continuation in part of our application Ser. No. 412,354 filed Nov. 2, 1973, now abandoned.

This invention relates to therapeutic compositions and in particular to compositions comprising phthalazine derivatives.

The present invention provides therapeutic compositions comprising a compound of formula I

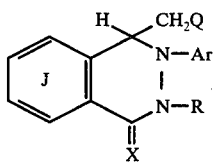

or its enol or enthiol form of formula Ia

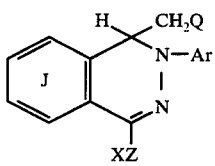

in which Q is COOH, CH$_2$OH or COOR$_6$, wherein R$_6$ is an ester forming group; X is oxygen or sulphur; R is hydrogen or alkyl; Z is hydrogen or acyl and Ar is an aryl group, and the ring J is optionally substituted, or pharmaceutically acceptable salts with inorganic and organic bases of those compounds which are acids, in admixture with a pharmaceutically acceptable diluent. Ar is preferably unsubstituted in the positions ortho to the point of attachment to the phthalazine ring.

The compounds of the compositions of the invention have valuable diuretic and saluretic properties in mammals. Accordingly, the invention also provides a method of inducing diuresis and saluresis in mammals which comprises administering to the mammal a pharmaceutically acceptable and effective amount of a compound described above.

Preferred compounds are those of formula II

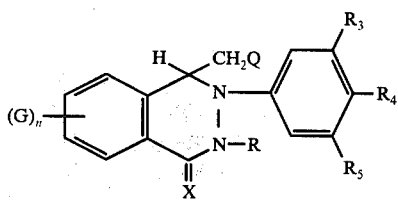

or their enol or enthiol forms of formula IIa

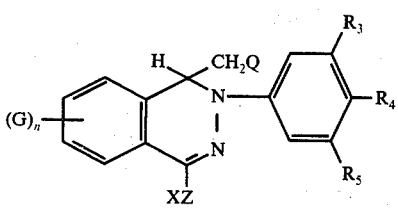

in which Q, X, R and Z are as previously defined; n is 0 to 4; each G may be the same or different and is selected from fluorine; chlorine; bromine; iodine; nitro; amino; substituted amino, e.g. dialkylamino and especially dimethylamino; cyano; alkyl, e.g. of 1 to 4 carbon atoms and especially methyl, ethyl and isopropyl; substituted alkyl, e.g. haloalkyl, especially trifluoromethyl; alkoxy, e.g. of 1 to 4 carbon atoms and especially methoxy; substituted alkoxy, e.g. aralkoxy, especially benzyloxy; alkylthio, e.g. of 1 to 4 carbon atoms and especially methylthio; alkylsulphonyl, e.g. mesyl; alkylsulphinyl, e.g. methylsulphinyl; hydroxy; aryl, e.g. phenyl and aroyl, e.g. benzoyl; and R$_3$, R$_4$, and R$_5$ may be the same or different and are selected from hydrogen; fluorine; chlorine; bromine; iodine; nitro; nitroso; cyano; isocyano; amino; substituted amino e.g. alkylamino, dialkylamino, arylamino, acylamino, hydroxyamino, arylidenamino, alkylidenamino, ureido, carbazoylamino, hydrazino, thioureido, thiocarbazoylamino, alkylsulphinylamino, alkoxycarbonylamino, sulphamoylamino and sulphonamido, e.g. alkyl-, substituted alkyl- and arylsulphonamido; alkyl, e.g. of 1 to 7 carbons and especially methyl, ethyl, propyl, isopropyl and t-butyl; substituted alkyl, e.g. haloalkyl, especially trifluoromethyl, aralkyl, e.g. benzyl, hydroxyalkyl, e.g. hydroxypropyl and alkoxyalkyl, e.g. methoxymethyl; cycloalkyl, e.g. cyclohexyl and substituted cycloalkyl; alkenyl e.g. allyl; aryl e.g. phenyl and substituted phenyl e.g. tolyl, alkoxyphenyl and halophenyl; cycloalkenyl, e.g. cyclohexenyl; alkoxy, e.g. of 1 to 4 carbons and especially methoxy, ethoxy, n-propoxy, isopropoxy and butoxy; substituted alkoxy, e.g. dialkylaminoalkoxy and aralkoxy, alkenyloxy, e.g. allyloxy and butenyloxy; cycloalkyloxy, e.g. cyclohexyloxy; cycloalkenyloxy, e.g. cyclohexenyloxy; acyloxy, e.g. acetoxy; alkylthio e.g. of 1 to 4 carbons and especially methylthio, ethylthio and propylthio; substituted alkylthio e.g. haloalkylthio; especially trifluoromethylthio, and aralkylthio; alkenylthio; cycloalkylthio; cycloalkenylthio; arylthio, e.g. phenylthio; alkylsulphonyl, e.g. mesyl; alkylsuphinyl, e.g. methylsuphinyl; acyl e.g. acetyl and propionyl; substituted acyl, especially haloacyl, e.g. trifluoroacetyl; aroyl, e.g. benzoyl; heteroaroyl, e.g. 2-thenoyl; hydroxy; mercapto; carbamoyl; thiocarbamoyl; sulphamoyl; substituted sulphamoyl, e.g. dialkylsulphamoyl, especially dimethylsulphamoyl and diethylsulphamoyl; substituted and unsubstituted heterocyclic rings, e.g. 2-, 3- and 4- pyridyl, piperidino, morpholino, thiamorpholino, pyrrolin-1-yl, pyrrolidin-1-yl, 1-pyrrolyl, 2-thienyl, 2-thiazolyl, 2-oxopiperidino, 5-oxopyrazolidinyl, optionally, N-alkylated, and 2-oxopyrrolidin-1-yl. R$_3$ and R$_4$ may also together form a portion or a carbocyclic or heterocyclic ring fused to the benzene ring, which rings may be substituted, e.g. with one or more lower alkyl groups.

When G, R$_3$, R$_4$ or R$_5$ is substituted amino, the nitrogen of the amino group may be mono or disubstituted, with at least one of the substitutes preferably being an alkyl, e.g. methyl, ethyl or isopropyl, or an alkoxy group, e.g. methoxy. Where the substituent on the substituted amino group is itself an amino group or is one containing further amino groups, e.g. ureido, these further amino groups may also be mono- or di- substituted, usually alkyl, e.g. methyl-, substituted.

Examples of substituted amino groups include methylamino, ethylamino, dimethylamino, diethylamino, methylethylamino, trimethylammonio, anilino, benzylamino, N-methylformamido, N-methylacetamido, methanesulphonamido, anesulphonamido, N-methyl-methanesulphonamido, N-methyl-p-toluenesulphonamido and N-acetyl-N',N'-dimethylhydrazino.

Examples of fused ring systems include the following. Unless otherwise shown, these are attached to the 2-nitrogen of the phthalazine ring at either the 5 or the 6 position (in the case of 9-membered bicyclic ring systems and usually the 5 position) or at the 6 or the 7 position (in the case of the 10-membered bicyclic ring systems). The first four of these systems are particularly preferred.

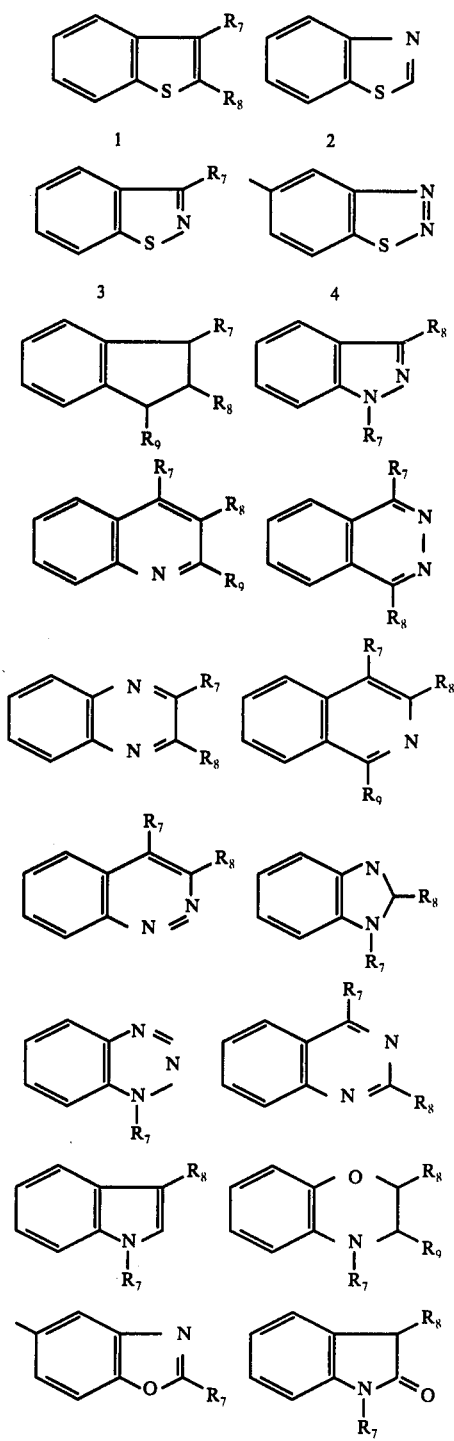

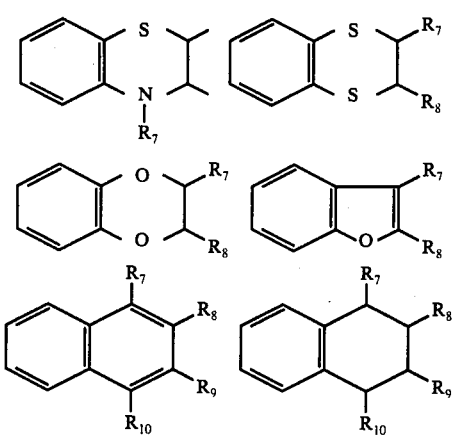

$R_7$, $R_8$, $R_9$ and $R_{10}$ are the same or different and are hydrogen or lower alkyl, e.g. methyl.

Especially preferred systems are the following:

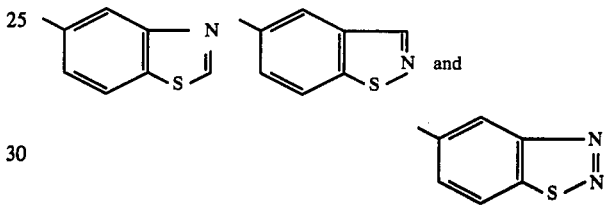

and of these the third is particularly preferred.

$R_5$ is preferably hydrogen. $R_3$ is preferably other than hydrogen. R may be alkyl of, for example 1 to 7 carbon atoms, preferably 1 to 3 carbon atoms and especially methyl or ethyl. It is generally preferred however that R is hydrogen except when one or more of $R_3$, $R_4$ and $R_5$ is a substituted or unsubstituted amino group. Q is usually COOH, but when it is $COOR_6$, $R_6$ is preferably an alkyl group, e.g. methyl or ethyl, although other ester-forming groups for example alkyloxyalkyl, acyloxyalkyl, e.g. pivaloyloxymethyl, and 6-indanyl may be suitable. X is preferably oxygen.

Preferred compositions are those containing compounds of formula II or IIa wherein Q is selected from the group consisting of COOH and $CH_2OH$, R is selected from the group consisting of hydrogen and $C_{1-7}$ alkyl, Z is hydrogen or acetyl, $R_5$ is hydrogen, $R_3$ and $R_4$ are each independently selected from the group consisting of hydrogen, fluorine, chlorine, bromine, iodine, nitro, cyano, $C_{1-7}$ alkyl, trifluoromethyl, 1-hydroxypropyl, methoxymethyl, phenyl, $C_{1-4}$ alkoxy, $C_{1-4}$ alkylthio, trifluoromethylthio, phenylthio, methylsulphonyl, methylsulphinyl, acetyl, propionyl, trifluoroacetyl, benzoyl, thenoyl, hydroxy, sulphamoyl, N,N-dimethylsulphamoyl, N,N-diethylsulphamoyl, amino, N-methylamino, N,N-dimethylamino, N-ethylamino, N,N-diethylamino, N,N-methylethylamino, N-methylformamido, N-methylacetamido, N-methylmethanesulphonamido, N-methyl-p-toluenesulphonamido, 1-pyrrolyl, or $R_3$ and $R_4$ together form a portion of a heterocyclic ring fused to the benzene ring to form a group selected from the group consisting of:

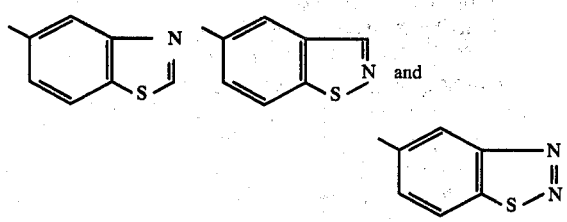

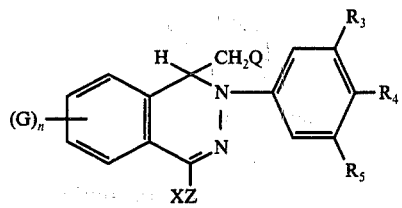

wherein n is 0 or 1 and G is in the 7-position and is selected from the group consisting of fluorine, chlorine, bromine, $C_{1-4}$ alkyl, $C_{1-4}$ alkylthio and $C_{1-4}$ alkoxy or is in the 6 position and is fluorine, or a pharmaceutically acceptable ester or salt of those compounds in which Q is COOH; said compound being in admixture with a pharmaceutically acceptable carrier. Preferably, n is 1 or 2, and most preferably 1, in which case G is preferably in the 7-position.

Particularly preferred groups which G may be included methyl, ethyl and methoxy, as well as isopropyl, fluorine, chlorine and bromine.

A particularly preferred group of compounds are those in which $R_5$ is hydrogen, n is 1 and G is in the 7-position, Q is carboxy, X is oxygen, $R_4$ is hydrogen and $R_3$ is other than hydrogen or $R_3$ and $R_4$ together form a portion of a heterocyclic ring fused to the benzene ring, as well as salts thereof.

Especially preferred of this group of compounds are those in which G is chlorine, methyl, ethyl, isopropyl or methoxy and when R (or Z) is hydrogen, $R_3$ is nitro, trifluoromethyl, methylthio, chloro or bromo or $R_3$ and $R_4$ together with the benzene ring to which they are attached are benzothiazol-5-yl, 1,2,3-benzothiadiazol-5-yl or 1,2-benzoisothiazol-5-yl and when R is methyl, $R_3$ is N,N-dimethylamino.

When $R_3$ is not part of a fused ring system it is particularly preferred that it is trifluoromethyl, trifluoroacetyl, N,N-dimethylamino or methylthio and especially trifluoromethyl.

NOVEL COMPOUNDS

Many of the compounds of the invention are novel. The invention thus also provides compounds of formula I or Ia in which Q, X, R, Z and Ar are as previously defined with the proviso that when the ring J is unsubstituted, (i) Q is COOH, COOMe, or COOEt, X is oxygen, and R is hydrogen or methyl then Ar is not phenyl, m or p-chlorophenyl, m or p-nitrophenyl, p-(p-nitrophenylazo)phenyl or p-phenylazophenyl or (ii) when Q is COOH, X is oxygen and R is hydrogen then Ar is not m or p-anilino or m- or p-acetamidophenyl.

Preferred compounds are those of formula II

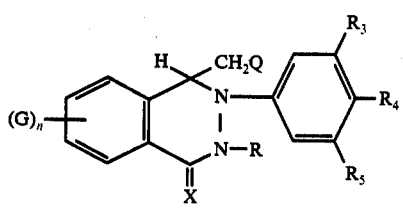

or their enol or enthiol form of formula IIa in which G, n, Q, X, Z, $R_3$, $R_4$ and $R_5$ are as herein defined, with the proviso that when (i) n is O, Q is COOH, COOMe, COOEt, X is oxygen, R is hydrogen or methyl and one of $R_3$ and $R_4$ is H, Cl or $NO_2$ or $R_4$ is phenylazo or p-nitrophenylazo, or (ii) n is O, Q is COOH, X is oxygen, R is hydrogen and one of $R_3$ and $R_4$ is amino or acetamido, then at least two of $R_3$, $R_4$ and $R_5$ are groups as defined for $R_3$, $R_4$ and $R_5$ other than hydrogen, together with pharmaceutically acceptable salts with inorganic and organic bases of these compounds which are acids.

A particularly suitable group of novel compounds are those in which Q is a carboxyl group, n is 1 and G is in the 7-position and is selected from the group consisting of fluorine, chlorine, bromine, $C_{1-4}$ alkyl, $C_{1-4}$ alkoxy and $C_{1-4}$ alkylthio, R is hydrogen or $C_{1-7}$ alkyl, $R_5$ is hydrogen and $R_3$ and $R_4$ together with the benzene to which they are attached form one of the three preferred fused ring systems mentioned above, together with pharmaceutically acceptable salts and esters of these compounds.

Another particularly suitable group of novel compounds are those in which Q is a carboxyl group, n is 1 and G is in the 7-position and is selected from the group consisting of fluorine, chlorine, bromine, $C_{1-4}$ alkyl, $C_{1-4}$ alkoxy and $C_{1-4}$ alkylthio, R is hydrogen or $C_{1-7}$ alkyl. $R_4$ and $R_5$ are hydrogen and $R_3$ is trifluoromethyl, trifluoroacetyl, or N,N-dimethylamino, methylthio and especially trifluoromethyl.

Of these two groups of preferred compounds it is particularly preferred that when G is alkyl it is selected from methyl, ethyl, n-propyl and isopropyl, when G is alkoxy it is methoxy, when G is alkylthio it is methylthio and when R is alkyl it is methyl or ethyl.

Examples of suitable salts include the sodium salt and suitable esters are $C_{1-7}$ alkyl esters especially methyl or ethyl esters.

PREPARATION OF COMPOUNDS

The preferred compounds of the invention may be prepared by a process which comprises the steps of
(a) reacting a 2-naphthol-1-sulphonic acid of formula III

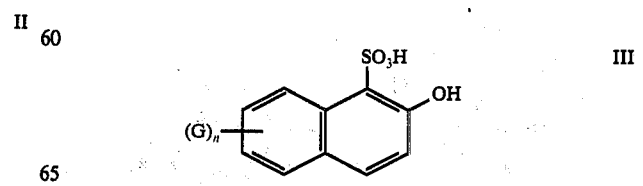

or a salt thereof in which G and n are as previously defined with a compound of formula IIIa

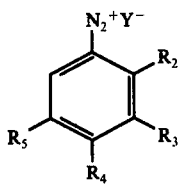

IIIa in which $R_3$, $R_4$ and $R_5$ are as previously defined, $R_2$ is hydrogen, iodine, bromine or chlorine and Y is the anion of a mineral acid, (b) treating the product from (a) with a mild base,
(c) treating the product from (b) with an alkali metal hydroxide, followed by acidification to give a compound of formula IV.

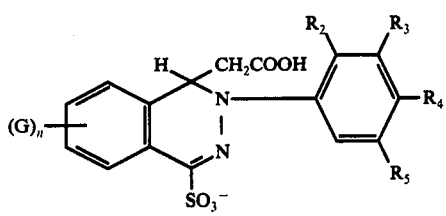

IV (d) if desired, modifying at least one of the groups G, $R_3$, $R_4$ or $R_5$ and/or, if $R_2$ is iodine, bromine or chlorine, converting it to hydrogen, and/or converting the 1-acetic acid group to a hydroxyethyl group,
(e) treating the product from (c) or (d) with an aqueous acid or an alcoholic acid to give a compound of formula II in which R is hydrogen and X is oxygen,
(f) in the case when $R_2$ is iodine, bromine or chlorine, converting it to hydrogen,
(g) in the case when the compound obtained from (d), (e) or (f) is one falling within the proviso, mentioned above, modifying at least one of the groups Q, X, Z, R, $R_3$, $R_4$ or $R_5$ to give a compound not falling within the proviso,
(h) if desired, modifying at least one of the groups Q, X, Z, G, R, $R_3$, $R_4$ or $R_5$ in the product obtained from (f) and (g), and
(i) if desired, forming a pharmaceutically acceptable salt with an inorganic or organic base of any compound which is an acid.

Steps (e) to (i) need not always be carried out in the order given. Thus, for example where the $R_2$ group is halogen it may, in some cases, be converted to hydrogen after modification of one or more of the groups G, $R_3$, $R_4$, $R_5$ or Q, or even simultaneously, when, for instance, such a modification includes a hydrogenation step. Similarly, for example, it may be desirable to carry out steps (d) and (e) simultaneously; for instance conversion of the 1-acetic acid group to a hydroxyethyl group may be carried out at the same time as the hydrolysis of the 4-sulphonate group.

It will also be appreciated that it is not necessary to isolate the products from one step before proceeding with the next step.

The compounds of formula III in which $n$ is greater than 0 and their salts are novel and may be prepared by sulphonating the substituted 2-naphthol, e.g. by treatment with concentrated sulphuric acid, usually at low temperature, preferably $-10$ to $+10°$ C. The sulphonate salts may then be obtained by treating the sulphonic acid so obtained with an inorganic salt, e.g. sodium chloride.

Without wishing to be held to any theory we believe that the reaction for preparing the compounds of formula II proceeds by the following sequence:

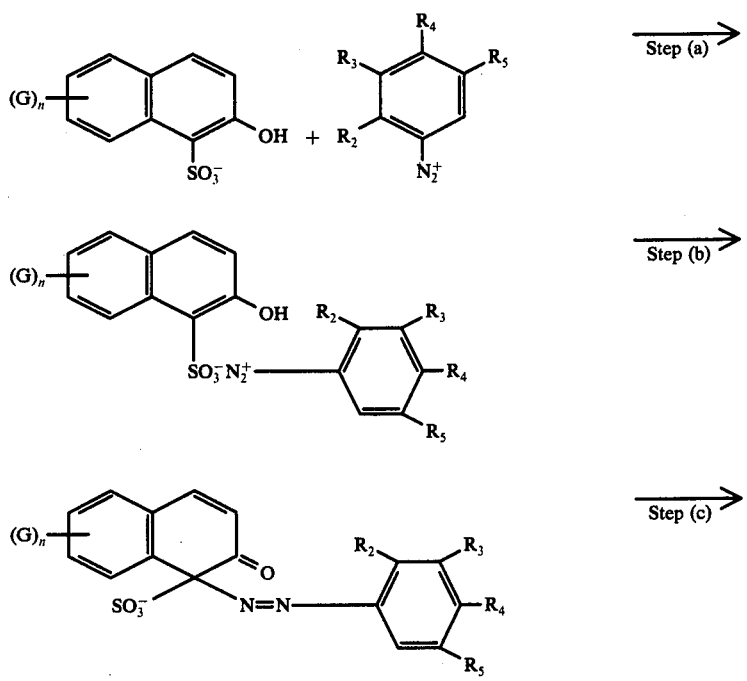

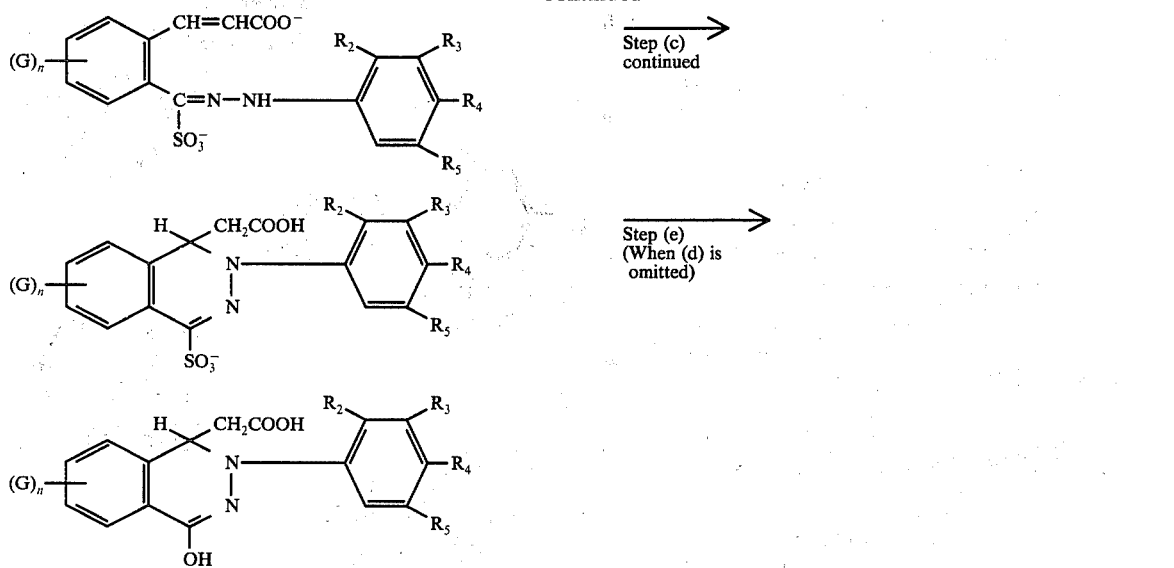

Step (a) is generally carried out at a temperature below 60° C., preferably from −20 to +50° C., e.g. −10 to +10° C. The salt is preferably an alkali metal salt, e.g. the sodium salt and Y is preferably Cl.

Step (b) is generally carried out at a temperature of from −20 to +20° C., e.g. −10 to +10° C. The mild base is generally an alkali metal carbonate or ammonium carbonate and is preferably sodium carbonate. The period of the reaction mainly depends on the nature of the substituents in the compounds of formula III. Those compounds in which at least one of $R_2$, $R_3$, $R_4$ or $R_5$ is an electron withdrawing substituent, e.g. halogen and trifluoromethyl, generally only require a short reaction time, e.g. 1 to 30 minutes. These compounds in which at least one of $R_2$, $R_3$, $R_4$ or $R_5$ is an electron donating substituent, e.g. alkyl, generally require a longer reaction time, e.g. ½ to 24, preferably 1 to 6 hours.

Step (c) is generally carried out at a temperature of from −20 to +50° C., e.g. −5 to +30° C. The alkali metal hydroxide is generally sodium hydroxide. The period of reaction is generally between 1 and 24 hours.

Step (e) is generally carried out at a temperature for example, of from 20° to 200° C., preferably 50° to 120° C., and if desired, under reflux. The acid is usually a mineral acid, for example hydrochloric acid. The time of reaction is usually at least ½ an hour e.g. 1 to 6 hours. When the acid is used in conjunction with an alcohol, the acid is usually anhydrous e.g. hydrochloric acid gas, which is dissolved in the alcohol e.g. methanol or ethanol. The product obtained is then one in which Q is $COOR_6$.

Compounds in which R is alkyl are generally obtained by alkylation of the compounds in which R is hydrogen. Suitable alkylating agents include alkyl halides, e.g. methyl or ethyl iodide or propyl bromide, and dialkyl sulphates, e.g. dimethyl or diethyl sulphate. The alkylation is preferably carried out in the presence of a base, e.g. an alkali metal hydroxide in which case when it is desired to obtain the acid, acidification, e.g. with hydrochloric acid may be carried out. When using an alkyl halide the reaction is generally carried out on a metal derivative which can be preformed, for example by the use of a metal hydride, e.g. sodium hydride. The alkylation may be carried out at a temperature of, for example from 0° to 200° C., preferably in the presence of a solvent, e.g. tetrahydrofuran or diglyma.

To obtain compounds in which X is sulphur, it is usually necessary to sulphurise the compound in which X is oxygen. This may be carried out with a sulphurising agent, for example phosphorus pentasulphide. This reaction may be carried out, for example at a temperature of from 20° to 100° C. Generally the compound of formula II is converted to an ester before sulphurisation. If the free acid is required this can then be obtained from the sulphurised esters by hydrolysis.

When $R_2$ is a halogen group it is replaced with hydrogen, generally by hydrogenation in conventional manner, for example using a palladium-charcoal catalyst preferably in the presence of a salt of a weak acid, e.g. sodium acetate.

Examples of modifications to one or more of G, $R_3$, $R_4$ and $R_5$ that may be carried out include the following, where the radicals shown may be examples of G, where applicable, and of $R_3$, $R_4$, and $R_5$. A particularly useful modification is reductive alkylation of a nitro or amino group, examples of which are shown under c, d, f and g.

$$\begin{array}{lll}
-Br \\ -I
\end{array} \Bigg\} \xrightarrow{\text{Metal cyanide}} -CN \qquad \text{a)}$$

$$-NO_2 \xrightarrow{H_2/Pd-C} -NH_2 \qquad \text{b)}$$

$$-NO_2 \xrightarrow[H_2/Pd-C]{HCHO} -NMe_2 \qquad \text{c)}$$

$$-NO_2 \xrightarrow[H_2/Pd-C]{CH_3CHO} -NEt_2 \qquad \text{d)}$$

$$-NH_2 \xrightarrow[KOH]{Me_2SO_4} -NMe_2 \qquad \text{e)}$$

$$-NH_2 \xrightarrow[H_2/Pd-C]{HCHO} -NMe_2 \qquad \text{f)}$$

$$-NH_2 \xrightarrow[H_2/Pd-C]{CH_3CHO} -NHEt \qquad \text{g)}$$

$$\xrightarrow[H_2/Pd-C]{HCHO} -NMeEt$$

$$-NH_2 \xrightarrow{MeSO_2Cl} -NHSO_2Me \qquad \text{h)}$$

$$\xrightarrow[K_2CO_3]{Me_2SO_4} -N(Me)SO_2Me$$

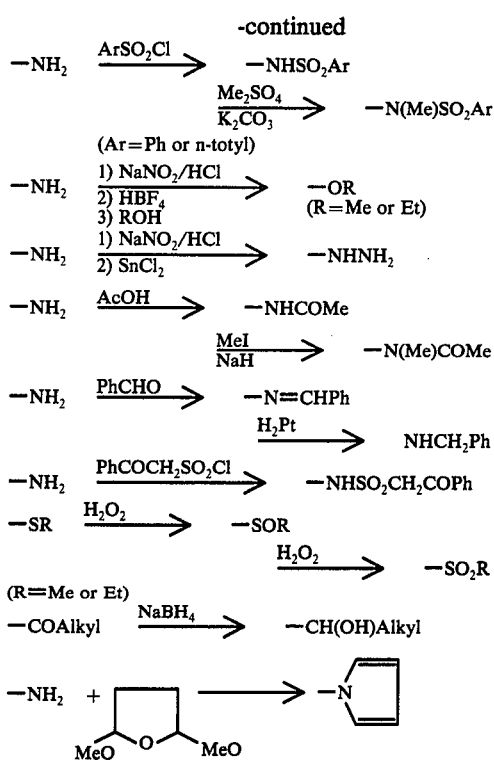
In some cases fused rings may be obtained by suitable modification of $R_3$ and $R_4$ so that they cyclise to form the fused ring. Examples of such reactions include the following:
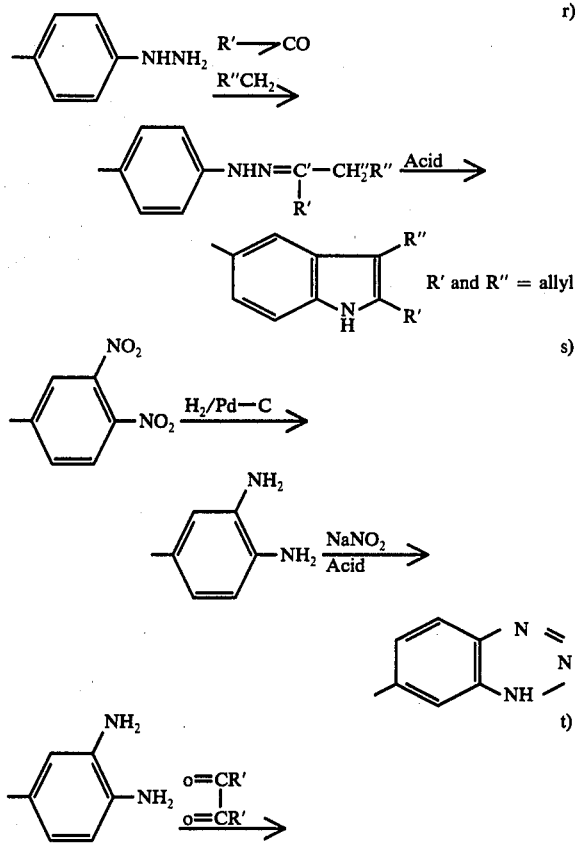
i)
j)
k)
l) (from s)
m)
n)
o)
p)
q)
r)
s)
t)
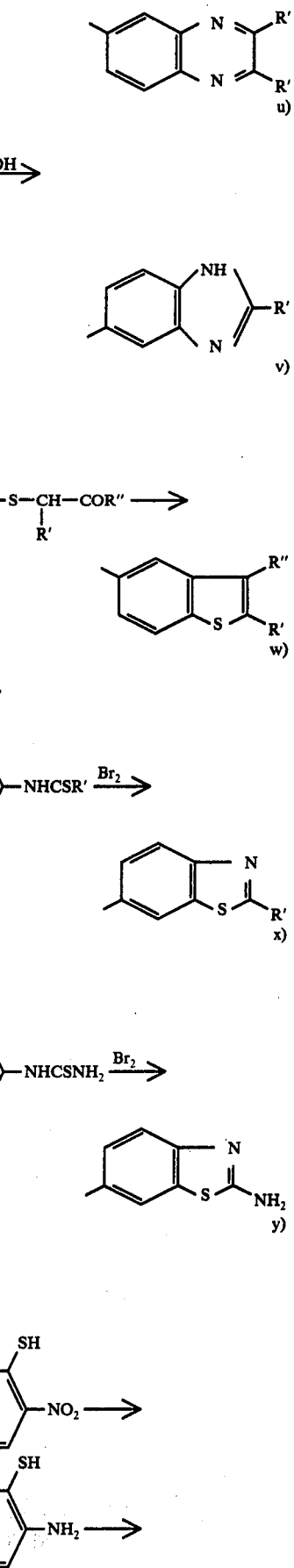
u)
v)
w)
x)
y)

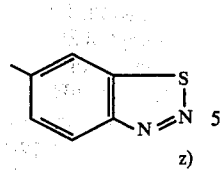

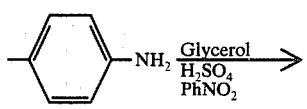

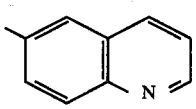

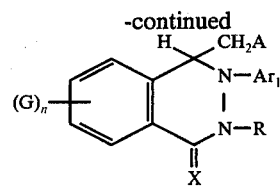

The conversion of compounds in which Q is COOH to those in which Q is CH₂OH may be carried out by various procedures. When R is alkyl, the compound may be converted to a mixed anhydride e.g. by reacting with an ester of a haloformic acid, usually ethyl chloroformate, in the presence of a tertiary amine, e.g. triethylamine. The mixed anhydride is then reduced with, for example, sodium borohydride. When the group in the 4-position of the phthalazine nucleus is a hydroxy or mercapto group it may be first necessary to protect it before carrying out this procedure, e.g. by acylation, usually acetylation, or by treatment with an agent such as benzyl chloroformate to form the 4-benzloxycarbonyloxy compound. The protecting group can then be removed by conventional means, e.g. by hydrolysis in the case of the acetyl group or hydrogenation in the case of the benzyloxycarbonyl group. Alternatively when R is hydrogen or alkyl, acids may be converted to the corresponding acid chloride, e.g. by reaction with thionyl chloride, which can then be reduced, for example using lithium aluminium tri-t-butoxy hydride. When converting compounds in which the group in the 4-position of the phthalazine nucleus is a sulphonate, i.e. compounds of formula IV, the procedure used is generally the formation and reduction of the mixed anhydride.

Salts of acids may be obtained by reacting the acids with organic or inorganic bases.

O- or S-acylated derivatives may be obtained by treating the compounds in which R is hydrogen with an acylating agent e.g. acetyl chloride or acetic anhydride.

If desired, compounds in which Q is CH₂OH may be oxidised, in conventional manner, to give compounds in which Q is COOH. Also compounds in which Q is COOR₆ may be hydrolysed, in conventional manner, to give compounds in which Q is COOH or salts of such compounds.

It will thus be appreciated that compounds of the invention may be prepared by a process in which a compound of formula VI or VIa

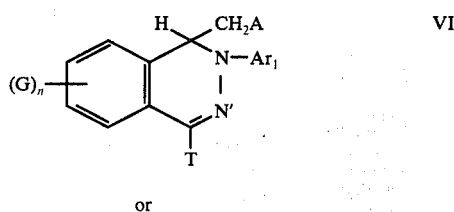

or in which A is the group Q as previously defined or a group convertible to Q; G₁ is the group G as previously defined or a group convertible to G; Ar₁ is aryl; T is the group XZ as previously defined, or is SO₃⁻, and R and Z are as previously defined; is treated to modify at least one of the groups A, G₁, Ar₁, R, X, T or Z to give a novel compound of the invention.

Examples of groups convertible to Q include an aldehyde group which may be oxidised to give COOH to a cyano or carbamoyl group which may be hydrolysed to give COOH.

It will be appreciated that, since the compounds of the invention possess an asymmetric carbon atom, they are ordinarily present in the form of a racemic mixture. The resolution of such racemates may be carried out by conventional means and the separated optically active stereoisomers form part of the present invention.

DETERMINATION OF PHARMACOLOGICAL ACTIVITY

The therapeutic activity of compounds of the invention can be assessed in various species, by administering the drug to the animal and measuring the amount of sodium ions in the urine excreted after a given time (usually expressed as milliequivalents of sodium ions/kg. of body weight of the animal). In rats, the drug was administered orally in suspension in distilled water containing 0.25% hydroxyethyl cellulose and the amount of sodium ions in the urine was compared with the amount in control rats given the same amount of liquid without any drug. In this test 4-hydroxy-7-methyl-2-(3-methylthiophenyl)-1,2-dihydrophthalazine-1-acetic acid (or in its "keto" form, 7-methyl-2-(3-methylthiophenyl)-4-oxo-1,2,3,4-tetrahydrophthalazine-1-acetic acid) promoted sodium ion loss and had a potency based on sodium ion diuresis better than that of frusemide.

METHODS OF ADMINISTRATION

The compounds may be administered in conventional manner for example, orally, rectally or parenterally, preferably orally. The optium dosage rate varies inter alia with the route of administration and the condition being treated, but normally lies within the range 0.003–100, e.g. 0.1–100 mg./kg./day. The unit dose may vary from 0.1 mg – 500 mg., e.g. 3 mg. to 500 mg; for oral administration the dosage rate is preferably 0.1 mg. – 2g. e.g. 3 mg. – 2g. per subject per day.

For ease of administration the compounds are preferably formulated as therapeutic compositions which comprise the active compound in association with pharmaceutical excipients for the production of compositions for oral, rectal or parenteral administration. These compositions preferably contain 0.1–90% by weight of a compound of the invention.

Preferred compositions of the invention are compositions for oral administration, and these are the conventional pharmaceutical forms for such administration, such as for example tablets, capsules, lozenges, powders, effervescent granules, syrups and aqueous and oily suspensions. The excipients used in the preparation of these compositions are the excipients of the pharmacist's art. Thus in the preparation of tablets, typical excipients include disintegrating agents, e.g. maize starch and lubricating agents, e.g. magnesium stearate. In the preparation of capsules, standard gelatin capsules may be used containing the active ingredient alone or admixed with a diluent. The liquid compositions may comprise as excipients water and sucrose to provide syrups, water, dispersing agents and suspending agents, e.g. sodium carboxymethylcellulose to provide aqueous suspensions, and a non-toxic oil, e.g. a vegetable oil such as arachis oil and a suspending agent to provide oily suspensions.

Other compositions of the invention are compositions for rectal administration, and these are the conventional pharmaceutical forms for such administration, such as for example suppositories with fatty glyceride or polyethylene glycol bases.

Compositions for parenteral administration are the conventional pharmaceutical forms for such administration, for example a sterile solution of the sodium salt in water.

In some formulations it may be beneficial to use the compounds of the invention in the form of particles of very small size, such as for example, as obtained by fluid energy milling, e.g. micronizing.

The active compounds may be mixed with or used in conjunction with other therapeutic agents, for example other diuretic agents, especially those which reduce potassium ion excretion e.g. amiloride, spironolactone or triamterene; and antihypertensive agents, such as reserpine or adrenergic neurone blocking agents, such as guanethidine or methyldopa. The compounds may additionally or alternatively be mixed or used in conjunction with a potassium salt, such as potassium chloride, to replace excess potassium loss that may result from the use of the diuretic compound. Generally the potassium salt is enterically coated.

This invention is illustrated in the following examples in which "parts" and "percentages" are by weight unless otherwise stated. In the examples the following abbreviations are used: "TPA" = 1,2,3,4-tetrahydrophthalazine-1-acetic acid. "TPAE" = 1,2,3,4-tetrahydrophthalazine-1-acetate. "DPA" = 1,2-dihydrophthalazine-1-acetic acid. "DPAE" = 1,2-dihydrophthalazine-1-acetate. "IMS" = Industrial methylated spirits.

The products of the examples gave satisfactory elemental analyses.

EXAMPLE I

A solution of 3-trifluoromethylaniline (80.5 g.; 0.5 mol) in a warm mixture of concentrated hydrochloric acid (200 ml.) and water (600 ml.) was cooled to 0° C. forming a mass of pale pink crystals. An ice-cold solution of sodium nitrite (41.5 g.) in water (75 ml.) was added over 10 minutes with stirring and continual cooling. This produced a clear yellow solution to which an ice-cold filtered solution of sodium 2-hydroxynaphthalene-1-sulphonate (162 g. of 80% pure) in water (1250 ml.) was added over 15 minutes. After another 15 minutes the brown precipitate which formed was collected, washed with ice-cold saturated brine (3 liters) and stirred with water (1 liter) at 0° C. Anhydrous sodium carbonate (150 g.) was quickly sprinkled in and after 1–2 minutes an ice-cold solution of sodium hydroxide (300 g.) in water (600 ml.) was added. The deep red solution was kept at 20° C. for 16 hours, carefully acidified to pH 6 with concentrated hydrochloric acid and then brought to pH 8 with saturated aqueous sodium carbonate. A small amount of dark azo by-product was filtered off and the sulphonate intermediate (Intermediate A) was precipitated by acidification to pH 1–2. This was filtered off, dissolved in hot water (600 ml.) and boiled under reflux for 2 hours, during the first 30 minutes of which concentrated hydrochloric acid (200 ml.) was added dropwise. After cooling to 0° C., the sticky brown solid which formed was separated and stirred with saturated aqueous bicarbonate (600 ml.) and ether (200 ml.). The ether layer was discarded and the aqueous layer was acidified to pH 1 with concentrated hydrochloric acid. The precipitate which formed was separated and recrystallised from a 1:2 mixture of acetic acid and water and then from ether, to give cream coloured prisms of 4-hydroxy-2-(3-trifluoromethylphenyl)-DPA, m.p. 194°–195° C.

EXAMPLES 2–43

By similar methods there were obtained from the appropriate anilines the corresponding acetic acids. In Examples 2–6, 9 and 17 a similar reaction time of 1–2 minutes was employed after addition of sodium carbonate but before addition of sodium hydroxide. In all the other Examples the reaction time was extended to 1 to 4 hours. In some cases, an oil was obtained instead of a precipitate after addition of the sodium 2-hydroxynaphthalene-1-sulphonate and in such cases this was washed with brine by decantation. Also in some cases, the sulphonate intermediate (intermediate A) was extracted into ethyl acetate and the extracts evaporated to dryness before being hydrolysed. Finally the crude product, in some cases, was purified by extraction with ether in a Soxhlet apparatus instead of crystallisation from aqueous acetic acid.

The compounds obtained are set out in Table I

TABLE I

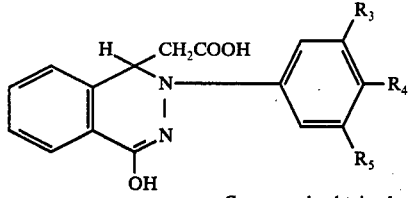

| Ex. No. | Aniline | $R_3$ | $R_4$ | $R_5$ | m.p. (° C) |
|---|---|---|---|---|---|
| 2 | 4-methyl-3-nitro | $NO_2$ | | Me | H | 226–229 |
| 3 | 3-fluoro | F | H | H | 258 |
| 4 | 3-bromo | Br | H | H | 193–195 |
| 5 | 3-methyl-sulphonyl | $MeSO_2$ | H | H | 143–144 |
| 6 | 4-trifluoro-methyl | H | $CF_3$ | H | 217–218 |
| 7 | 4-methyl | H | Me | H | 229–231 |
| 8 | 3-methyl | Me | H | H | 210–211 |
| 9 | 3-iodo | I | H | H | 180 |
| 10 | 3-methoxy | MeO | H | H | 178 |
| 11 | 3,4-dimethyl | Me | Me | H | 168–170 |
| 12 | 3-ethyl | Et | H | H | 126–127 |
| 13 | 3-ethoxy | EtO | H | H | 113–114 |
| 14 | 3-n-propoxy | nPrO | H | H | 101–103 |
| 15 | 3-iso-propoxy | isoPrO | H | H | 178–179 |
| 16 | 3-n-butoxy | nBuO | H | H | 171–172 |
| 17 | 3-chloro-4-methyl | Cl | Me | H | 184–185 |
| 18 | 4-ethyl | H | Et | H | 177–179 |
| 19 | 3-methylthio | MeS | H | H | 106–107 |
| 20 | 3-acetyl | MeCO | H | H | 129–130 |
| 21 | 3-cyano | —CN | H | H | 241–255 |
| 22 | 3-diethyl-sulphamoyl | $Et_2NSO_2$ | H | H | 188 |

TABLE I-continued

Structure: phthalazinone with N-aryl substituent bearing R₃, R₄, R₅

| Ex. No. | Aniline | R₃ | R₄ | R₅ | m.p. (° C) |
|---|---|---|---|---|---|
| 23 | 3-dimethyl-sulphamoyl | Me₂NSO₂ | H | H | 227 |
| 24 | 3-ethylthio | EtS | H | H | 87–88 |
| 25 | 3-phenyl | Ph | H | H | 75–90 |
| 26 | 3-benzoyl | PhCO | H | H | 147–150 |
| 27 | 3-phenylthio | PhS | H | H | 95–97 |
| 28 | 3-n-propylthio | PrS | H | H | 82–84 |
| 29 | 3-methoxymethyl | MeOCH₂ | H | H | 124–128 |
| 30 | 3-n-propionyl | EtCO | H | H | 130 |
| 31 | 3-n-propyl | Pr | H | H | 173–174 |
| 32 | 4-iodo | H | I | H | 231 |
| 33 | 3,4-dichloro | Cl | Cl | H | 217–218 |
| 34 | 3-chloro-4-methoxy | Cl | MeO | H | 227–229 |
| 35 | 4-bromo-3-fluoro | F | Br | H | 140–147 |
| 36 | 3-methyl-4-nitro | Me | NO₂ | H | 143–144 |
| 37 | 4-fluoro-3-trifluoromethyl | CF₃ | F | H | 187–188 |
| 38 | 4-chloro-3-methyl | Me | Cl | H | 220 |
| 39 | 3-methyl-5-nitro | Me | H | NO₂ | 251–252 |
| 40 | 3,5-dichloro | Cl | H | Cl | 240 |
| 41 | 4-chloro-3-nitro | NO₂ | Cl | H | 245–247 |
| 42 | 3-(2-thenoyl) | (2-thienyl-CO-) | H | H | 157 |
| 43 | 3-trifluoromethylthio | CF₃S | H | H | 192–193 |

EXAMPLES 44–47

In a similar way starting from the appropriate aromatic amine the acids set out in Table II were obtained.

TABLE II

| Ex. No. | Amine | Ar | m.p. (° C) |
|---|---|---|---|
| 44 | 1,2,3-benzothiadiazol-5-ylamine | (1,2,3-benzothiadiazol-5-yl) | 250 |
| 45 | benzo[b]thien-5-ylamine | (benzo[b]thien-5-yl) | 235–237 |
| 46 | benzothiazol-5-ylamine | (benzothiazol-5-yl) | 245–248 |
| 47 | 1,2-benzoisothiazol-5-ylamine | (1,2-benzoisothiazol-5-yl) | 245–246 |

EXAMPLE 48

The intermediate A (5g.) from Example 1 was suspended in dry methanol (250 ml.) and cooled to 0–5° C. Hydrochloric acid gas was passed in over 1 hour and the mixture allowed to stand for 3 days at room temperature. It was then evaporated under reduced pressure and the residue extracted with cyclohexane to give methyl 4-hydroxy-2-(3-trifluoromethylphenyl)-DPAE, m.p. 129°–30° C.

EXAMPLE 49

The product of Example 30 (2.5 g.) was dissolved in aqueous sodium hydroxide (1N; 100 ml.), sodium borohydride (2 g.) added and the mixture stirred at room temperature overnight. The mixture was treated with charcoal, filtered and the filtrate acidified. The precipitate was collected, washed with water, dried and recrystallised from ethyl acetate to give 4-hydroxy-2-[3-(1-hydroxypropyl)phenyl]-DPA, m.p. 163°–164° C.

EXAMPLE 50

A solution of 3-methyl-2-(3-nitrophenyl)-4-oxo-TPA (10g.) in tetrahydrofuran was hydrogenated with hydrogen (2230 ml.) in the presence of palladised charcoal (10%; 2 g.). The colourless solution was filtered and the filtrate evaporated to crystallisation to give white crystals of 2-(3-aminophenyl)-3-methyl-4-oxa-TPA, m.p. 220° C.

EXAMPLE 51

In a similar manner as described in Example 50 but using the methyl ester of the starting material of that Example, there was obtained methyl 2-(3-aminophenyl)-3-methyl-4-oxo-TPAE, m.p. 175° C.

EXAMPLE 52

Diethyl sulphate (8.4 ml.) was added dropwise to a stirred solution of 2-(3-nitrophenyl)-4-oxo-TAP (6.92 g.) in a solution of pottasium hydroxide (11 g.) in water (60 ml.). After 1 hour at room temperature a further portion of diethyl sulphate (8.5 ml.) was added and stirring continued for 2 hours. The solution was cooled to 0°–5° C., acidified to pH 1–2 with concentrated hydrochloric acid, and the gummy product isolated and washed with water by decantation. The gum was digested with cold saturated aqueous sodium carbonate, the mixture washed with ether and the aqueous phase was stirred with charcoal, filtered, and acidified to pH 1–2 at 0°–5° C with concentrated hydrochloric acid. The pale yellow solid was collected by filtration and recrystallised from ethyl acetate to give 3-ethyl-2-(3-nitrophenyl)-4-oxo-TPA, m.p. 218°–220° C.

EXAMPLE 53–54

To the product of Example 51 (5 g.) dissolved in IMS (200 ml.) was added aqueous formaldehyde (40%; 3.7 ml.) Palladium charcoal catalyst (10%Pd; 5 g.) was added and the mixture hydrogenated with hydrogen with shaking for 3 hours. The mixture was then boiled for 10 minutes, filtrated and the filtrate concentrated and stood at 0° C. overnight. The white solid which crystallised was recrystallised from methanol after treatment with charcoal to give methyl 2-(3-N,N-dimethylaminophenyl)-3-methyl-4-oxo-TPAE, m.p. 121° C. (Example 53).

In a similar manner but using the product of Example 52 as starting material there was obtained 2-(3-N,N-dimethylaminophenyl)-3-ethyl-4-oxo-TPA, m.p. 198° C. (Example 54).

EXAMPLE 55

In a similar manner to that described in Example 50, but using the product of Example 52 as starting material, there was obtained 2-(3-aminophenyl)-3-ethyl-4-oxo-TPA, m.p. 204°–206° C.

EXAMPLE 56–59

In a similar manner to that described in Example 53, but using acetaldehyde instead of formaldehyde, four compounds were treated to give products as follows:
(a) Methyl 3-methyl-2-(3-nitrophenyl)-4-oxo-TPAE gave methyl 2-(3-N,N-diethylaminophenyl)-3-methyl-4-oxo-TPAE, m.p. 117°–120° C. (Example 56).
(b) 3-Methyl-2-(3-nitrophenyl)-4-oxo-TPA gave 2-(3-N,N-diethylaminophenyl)-3-methyl-4-oxo-TPA, m.p. 177°–178° C. (Example 57).
(c) The product of Example 51 gave methyl 2-(3-N-ethylaminophenyl)-3-methyl-4-oxo-TPAE, m.p. 163°–164° C. (Example 58).
(d) The product of Example 55 gave 3-methyl-2(3-N-ethylaminophenyl)-4-oxo-TPA, m.p. 176°–177° C. (Example 59).

EXAMPLE 60–62

The product of Example 52 was esterified with methanol and concentrated sulphuric acid and the product was recrystallised from methanol to give methyl 3-ethyl-2-(3-nitrophenyl)-4-oxo-TPAE, m.p. 135°–136° C. (Example 60).

This was hydrogenated in a manner similar to that described in Example 50 to give methyl 2-(3-aminophenyl)-3-ethyl-4-oxo-TPAE, m.p. 191.5°–192° C. (Example 61).

This was then treated in a manner similar to that described in Example 53 to give methyl 2-(3-N,N-dimethylaminophenyl)-3-ethyl-4-oxo-TPAE, m.p. 141°–142° C. (Example 62).

EXAMPLE 63

To the product from Example 51 (2.0 g.) in pyridine (12 ml.) was added methane sulphonyl chloride (4 ml.). The solution was boiled under reflux for 1 hour and then poured onto an ice/water mixture. The tar which formed crystallised overnight and was then scratched with ethyl acetate after decanting off the aqueous phase. The pale yellow crystalline solid was filtered, washed with ethyl acetate and recrystallised from ethanol to give white crystals of methyl 2-(3-methanesulphonamidophenyl)-3-methyl-4-oxo-TPAE, m.p. 211° C.

To a solution of this product (2.3 g.) in acetone (50 ml.) was added potassium carbonate (30 g.) and dimethyl sulphate (2.5 g.). The resulting suspension was refluxed for two hours and then stood at room temperature overnight. The suspension was poured into an ice/water mixture and the precipitated solid extracted with chloroform. The extracts were washed with water, dried over magnesium sulphate and evaporated to dryness. The solid remaining was extracted with ether and the ether extracts were reduced in volume to give white crystals of methyl 3-methyl-2-(3-N-methylmethanesulphonamidophenyl)-4-oxo-TPAE, m.p. 132°–134° C.

EXAMPLE 64

To the product of Example 50 (3 g.) suspended in water (40 ml.) was added dropwise a mixture of dimethyl sulphate (8 g.) and aqueous potassium hydroxide (7 g. in 25 ml. of water). The solution obtained was stirred for 20 minutes, cooled to 0° C. and acidified with concentrated hydrochloric acid. A yellow gum formed which was dissolved in ethyl acetate after the supernatant liquid had been removed. The solution was treated with charcoal and then light pretroleum (b.p. 40°–60° C.) was added. The precipitate was dissolved in hot ether and light petroleum added until the solution became cloudy. It was then allowed to stand overnight when white crystals of 2-(3-N,N-dimethylaminophenyl)-3-methyl-4-oxo-TPA, m.p. 192° C., formed.

EXAMPLE 65

The product of Example 51 (2g.) was dissolved in glacial acetic acid (10 ml.) and refluxed for 4 hours. The liquid was then poured into an ice/water mixture and left at 0° C. overnight. The solid which formed was filtered off and recrystallised from aqueous acetic acid (2 parts acid: 1 part water). The solid product was heated in vacuo at 100° C. for three hours to dry it completely and give methyl 2(3-acetamidophenyl)-3-methyl-4-oxo-TPAE, m.p. 228° C.

This product (4.5 g.) was dissolved in a 2:1 mixture of tetrahydrofuran and dimethylformamide (50 ml.) and methyl iodide (14 g.) was added followed by sodium hydride (50% in oil; 1.8 g.). The mixture was heated to 80° C. for 24 hours. The solvent was then evaporated in vacuo, ether (25 ml.) was added and the mixture evaporated to dryness. The solid was recrystallised from a 2:1 mixture of acetic acid and water to give methyl 3-methyl-2-(3-N-methylacetamidophenyl)-4-oxo-TPAE, m.p. 125°–127° C.

The final product of Example 65 was hydrolysed by the addition of a mixture of aqueous sodium hydroxide and IMS. The mixture was allowed to stand for 1 hour at room temperature and the IMS then evaporated under reduced pressure. The remaining liquid was neutralised with dilute hydrochloric acid and the resulting precipitate extracted with ether. The extracts was reduced in volume and scratched and the resulting solid was recrystallised from IMS to give 3-methyl-2-(3-N-methylacetamidophenyl)-4-oxo-TPA, m.p. 249°–250° C.

EXAMPLE 67

The product of Example 51 (3 g.) was dissolved in pyridine (18 ml.) and benzene sulphonyl chloride added (6 ml.). This was refluxed for 1 hour and poured onto an ice/water mixture. The mixture was allowed to stand overnight at 0° C. and aqueous layer decanted off. Ethyl acetate was added to the remaining tar which on scratching crystallised. The crystals were filtered and recrystallised from ethanol to give methyl 2-(3-benzenesulphonamidophenyl)-3-methyl-4-oxo-TPAE, m.p. 204° C.

This was hydrolysed in a manner similar to that described in Example 66 to give 2-(3-benzenesulphonamidophenyl)-3-methyl-4-oxo-TPA, m.p. 233° C.

EXAMPLE 68

The product of Example 51 (3g.) was dissolved in dichloromethane (10 ml.), pyridine (1 ml.) added and the mixture cooled to 0° C. A solution of benzoylmethanesulphonyl chloride (2 g.) in dichloromethane (10 ml.) was added dropwise with stirring. Stirring was continued for an hour at 0° C. and overnight at room temperature. Water was added and the organic phase dried (magnesium sulphate), filtered and reduced in volume. The mixture was allowed to stand for 2 days, after which the crystals which formed were filtered and recrystallised from IMS to give methyl 2-(3-benzoylmethanesulphonamidophenyl)-3-methyl-4-oxo-TPAE, m.p. 188°–189° C.

This was hydrolysed in a manner similar to that described in Example 66 to give 2-(3-benzoylmethanesulphonamidophenyl)-3-methyl-4-oxo-TPA, m.p. 210°–211° C.

EXAMPLE 69

In a similar manner to that described in Example 67 using p-toluene sulphonyl chloride instead of benzene sulphonyl chloride there was obtained methyl 3-methyl-4-oxo-2-(3-p-toluenesulphonamidophenyl)-TPAE, m.p. 183° C.

This was then methylated with dimethyl sulphate in a manner similar to that described in Example 63 to give crude methyl 3-methyl-2-[3-(N-methyl-p-toluenesulphonamido)phenyl]-4-oxo-TPAE. This was then hydrolysed in a manner similar to that described in Example 66 to give 3-methyl-2-[3-N-methyl-p-toluenesulphonamido)phenyl]-4-oxo-TPA, m.p. 79°–81° C.

EXAMPLE 70

The product of Example 51 (5.7 g.) was diazotized using sodium nitrite and hydrochloride acid. Aqueous fluoroboric acid (42%; 3.9 ml.) in water (10 ml.) was added to give an orange precipitate of the diazonium fluoroborate which was filtered off, washed with ethanol and then ether. The solid was then mixed with ethanol and heated on a steam bath. Nitrogen was evolved and the solid dissolved. The red solution was poured into an ice/water mixture. A red tar formed which on standing overnight at 0° C. recrystallised. The solid was filtered off, washed with IMS and recrystallised from IMS to methyl 2-(3-ethoxyphenyl)-3-methyl-4-oxo-TPAE, m.p. 123°–125° C.

This was hydrolysed in a similar manner to that described in Example 66 to give 2-(3-ethoxyphenyl)-3-methyl-4-oxo-TPA, m.p. 154.5°–156° C.

EXAMPLE 71

In a similar manner in Example 70 but using methanol instead of ethanol to react with the fluoroborate there was obtained methyl 2-(3-methoxyphenyl)-3-methyl-4-oxo-TPAE, m.p. 133° C., which was hydrolysed to give 2-(3-methoxyphenyl)-3-methyl-4-oxo-TPA, m.p. 171°–173° C.

EXAMPLE 72

The product of Example 51 (5.7 g.) was diazotised using sodium nitrite and hydrochloric acid. The diazonium solution was poured into a solution of stannous chloride (16.8 g.) in hydrochloric acid (20 ml.). The precipitate which formed, was filtered, washed with water and IMS and recrystallised from IMS to give methyl 2-(3-hydrazinophenyl)-3-methyl-4-oxo-TPAE, m.p. 220° C.

EXAMPLE 73

The product of Example 51 (5 g.) was dissolved in IMS (200 ml.), benzaldehyde (0.5 g.) was added and the solution refluxed overnight. A further 0.5 g. of benzaldehyde was added followed by one hour reflux, then a further 0.5 g., followed by two hours reflux. The solution was allowed to stand overnight and evaporated under reduced pressure to 50 ml. The concentrate was allowed to stand at 0° C. to yield a white crystalline product which was recrystallised from IMS to give methyl 2-(3-benzylidenaminophenyl)-3-methyl-4-oxo-TPAE, m.p. 153°–153.5° C.

A solution of this product (2 g.) in dried tetrahydofuran was hydrogenated with hydrogen (130 ml.) using a platinium oxide catalyst (0.1 g.). The solution was filtered and evaporated under reduced pressure to give a gun which crystallised on scratching with ether. The product was recrystallised from IMS to give methyl 2-(3-N-benzyl-aminophenyl)-3-methyl-4-oxo-TPAE, m.p. 148°–150° C.

This was hydrolysed in a similar manner to that described in Example 66 to give 2-(3-N-benzylaminophenyl)-3-methyl-4-oxo-TPA, m.p. 192°–193° C.

EXAMPLE 74

The product of Example 2 (3.6 g.) was dissolved in an aqueous solution of potassium hydroxide (5 g. in 40 ml. of water) and stirred with dimethyl sulphate (1.5 ml.) for 5 hours. Further potassium hydroxide (5 g.) and dimethyl sulphate (1.5 ml.) was added and stirring continued for an hour. The product was isolated by acidification with hydrochloric acid and recrystallised from aqueous methanol to give 3-methyl-2-(4-methyl-3-nitrophenyl)-4-oxo-TPA, m.p. 178°–179° C.

EXAMPLES 75–79

In a similar manner to that described in Example 74 the products of various other previous examples were methylated to give the 3-methyl derivatives as follows:

EXAMPLE 75

The product from Example I gave 3-methyl-4-oxo-2-(3-trifluoromethylphenyl)-TPA, m.p. 190°–191° C.

EXAMPLE 76

The product from Example 33 gave 2-(3,4-dichlorophenyl)-3-methyl-4-oxo-TPA, m.p. 191°–192° C.

EXAMPLE 77

The product from Example 40 gave 2-(3,5-dichlorophenyl)-3-methyl-4-oxo-TPA, m.p. 225°–227° C.

EXAMPLE 78

The product from Example 36 gave 3-methyl-2-(3-methyl-4-nitrophenyl)-4-oxo-TPA, m.p. 191°–193° C.

EXAMPLE 79

The product from Example 43 gave 2-(1,2,3-benzo thiadiazol-5-yl)-3-methyl-4-oxo-TPA, m.p. 204°–205° C.

EXAMPLES 80–83

In a similar manner to that described in Example 52, various compounds were ethylated to give the 3-ethyl derivatives as follows:
(a) 2-(3-Chlorophenyl)-4-hydroxy-DPA gave 2-(3-chlorophenyl)-3-ethyl-4-oxo-TPA, m.p. 178°–179° C. (Example 80)
(b) The product of Example 1 gave 3-ethyl-4-oxo-2-(3-trifluoromethylphenyl)-TPA, m.p. 176°–178° C. (Example 81)
(c) The product of Example 2 gave 3-ethyl-2-(4-methyl-3-nitrophenyl)-4oxo-TPA, m.p. 253°–255° C. (Example 82)
(d) The product of Example 40 gave 2-(3,5-dichlorophenyl)-3-ethyl-4-oxo-TPA, m.p. 221°–222° C. (Example 83)

EXAMPLES 84–85

In a similar manner to that described in Example 50, two compounds were hydrogenated to give the products as follows:
(a) The product of Example 74 gave 2-(3-amino-4-methylphenyl)-3-methyl-4-oxo-TPA, m.p. 205°–206° C. (Example 84)
(b) The product of Example 82 gave 2-(3-amino-4-methylphenyl)-3-ethyl-4-oxo-TPA, m.p. 172°–174° C. (Example 85)

EXAMPLES 86–89

In a similar manner to that described in Example 53, four compounds were treated with formaldehyde and hydrogen to give the products as follows:
(a) The product of Example 82 gave 2-(3-N,N-dimethylamino-4-methylphenyl)-3-ethyl-4-oxo-TPA, m.p. 177°–180° C. (Example 86)
(b) The product of Example 78 gave 2-(4-N,N-dimethylamino-3-methylphenyl)-3-methyl-4-oxo-TPA, m.p. 188°–191° C. (Example 87)
(c) The product of Example 74 gave 2-(3-N,N-dimethylamino-4-methylphenyl)-3-methyl-4-oxo-TPA, m.p. 212°–213° C. (Example 88)
(d) The product of Example 58 gave methyl 2-(3-N-ethyl-N-methylaminophenyl)-3-methyl-4-oxo-TPAE, m.p. 123°–125° C. (Example 89)

EXAMPLE 90

The product of Example 1 was esterified with methanol in a similar manner to that described in Example 60 to give methyl 4-hydroxy-2-(3-trifluoromethylphenyl)-DPAE, m.p. 129°–130° C.

EXAMPLE 91

The product from Example 90 (1.21 g.) was dissolved in dry tetrahydrofuran (10 ml.) and sodium hydride (0.16 g.) added. When hydrogen evolution stopped the mixture was stirred and refluxed for 15 minutes. The mixture was cooled and propyl bromide (0.4 ml.) added. The mixture was stirred and refluxed overnight, cooled and poured into water. The product was extracted with dichloromethane, and the extracts washed with water dried and evaporated. The solid residue was recrystallised from light petroleum (b.p. 40°–60° C) to give methyl 4-oxo-3-propyl-2-(3-trifluoromethylphenyl)-TPAE, m.p. 97°–98° C. This was hydrolysed in a similar manner to that described in Example 66 to give 4-oxo-3-propyl-2-(3-trifluoromethylphenyl)-TPA, m.p. 185°–186° C.

EXAMPLE 92

The product of Example 75 was esterified with methanol in a similar manner to that described in Example 60 to give methyl 3-methyl-4-oxo-2-(trifluoromethylphenyl)-TPAE, m.p. 148°–149° C.

EXAMPLE 93

The product of Example 19 (1.5 g.) was dissolved in glacial acetic acid (7.5 ml.) and hydrogen peroxide (10.5 ml. of 3%) was added over 2 to 3 minutes. After 20 hours water (45 ml.) was added and the solution cooled to 0° C. The crystals which formed were filtered and the filtrate extracted with ethyl acetate. The extract was evaporated to dryness and the product dried. This was combined with the crystals above and then recrystalised from methanol to give 4-hydroxy-2-(3-methylsulphinylphenyl)-DPA, m.p. 252°–253° C.

EXAMPLE 94

The product of Example 1 (3.7 g.) was mixed with acetic anhydride (4.5 ml.) and acetic acid (8 ml.) and refluxed for 12 hours. The mixture was cooled and poured onto ice which gave a pale gum. This was washed with water and then dissolved in ether. The solution was dried, filtered and allowed to crystallise to give 4-acetoxy-2-(3-trifluoromethylphenyl)-DPA, m.p. 157°–158° C.

EXAMPLE 95

Ethyl chloroformate (3.05 g.) was added dropwise to a stirred solution of 4-acetoxy-2-(3-nitrophenyl)-DPA (4.25 g.) and triethylamine (2.4 g.) in dry diglyme (50 ml.) at −5° C. The mixture was stirred for a further 20 minutes, filtered to remove triethylamine hydrochloride and the filtrate added dropwise to a stirred solution of sodium borohydride (0.444 g.) in water 25 ml.), the temperature being maintained at below 15° C during the addition. The resultant solution was allowed to stand at room temperature overnight and then added to a mixture of water (250 ml.) and acetic acid (30 ml.). The solution was extracted with ether and the ether extracts were evaporated to give a yellow gum. This was dissolved in IMS (40 ml.) and concentrated hydrochloric acid (10 ml.) and refluxed for 17 hours. The mixture was then cooled, diluted with water (200 ml.) and extracted with methylene chloride. The extracts were evaporated and the yellow solid obtained was recrystallised from toluene to give 4-hydroxy-1-(2-hydroxyethyl)-2-(3-nitrophenyl)-1,2-dihydrophthalazine, m.p. 164°–165° C.

EXAMPLES 96–98

In a similar manner to that described in Example 95, three compounds were converted to the corresponding hydroxyethyl compounds to give the products as follows:
(a) 3-Methyl-2-(3-nitrophenyl)-4-oxo-TPA gave 1-(2-hydroxyethyl)-3-methyl-2-(3-nitrophenyl)-4-oxo-1,2,3,4-tetrahydrophthalazine, m.p. 183°–184° C. (Example 96)
(b) The product of Example 75 gave 1-(2-hydroxyethyl)-3-methyl-4-oxo-2-(3-trifluoromethylphenyl)-

1,2,3,4-tetrahydrophthalazine, m.p. 149°-150° C. (Example 97)

(c) The product of Example 81 gave 3-ethyl-1-(2-hydroxyethyl)-4-oxo-2-(3-trifluoromethylphenyl)-1,2,3,4-tetrahydrophthalazine, m.p. 139°- 141° C. (Example 98)

EXAMPLE 99

The product of Example 1 (3.5 g.) was dissolved in dry tetrahydrofuran (10 ml.) and triethylamine (2.8 ml.) added. The solution was cooled to −5° C and benzyl chloroformate (4.4 ml.) in dry tetrahydrofuran (5 ml.) added dropwise to produce a slurry which was stirred for ½ hour. The mixture was filtered and the filtrate added over ¾ hour to a stirred solution of sodium borohydride (1.1 g.) in water 30 ml.). Stirring was continued for 15 hours and the mixture then poured in acetic acid (30 ml.) and ice. The yellow oil produced was extracted with dichloromethane and the extracts washed with aqueous sodium bicarbonate and water, dried and evaporated, to give an oil which was dissolved in ethanol (50 ml.) and hydrogenated with hydrogen (80 ml.) in the presence of palladised charcoal (10%:60 mg). The mixture was filtered and the filtrate evaporated under reduced pressure to give a yellow oil which on addition of light petroleum (b.p. 40°-60° C) gave a gum. The petrol was decanted off and ethyl acetate was added to give a solid which on recrystallisation from a mixture of ethyl acetate and light petroleum (b.p. 40°-60° C) gave 4-hydroxy-1-(2-hydroxyethyl)-2-(3-trifluoro methyl-phenyl)-1,2-dihydrophthalazine, m.p. 183°-184° C.

EXAMPLE 100

The product of Example 51 (0.7 g) was mixed with 2,5-dimethoxy-tetrahydrofuran in glacial acetic acid (10 ml) and the mixture refluxed for 1½ hours. It was then cooled, poured into an ice/water mixture and extracted with dichloromethane. The extract was washed with aqueous sodium bicarbonate, dried and evaporated under reduced pressure to give methyl 3-methyl-4-oxo-2-[3-(1-pyrrolyl) phenyl]-TPAE, m.p. 174° C.

EXAMPLE 101

6-Bromo-2-naphthol (44 g) was added portionwise, with stirring, to concentrated sulphuric acid, cooled to 0° C. When the mixture had solidified, it was allowed to stand overnight at room temperature. Water (250 ml) was added and the mixture stirred and filtered. Sodium chloride (40 g) was added to the filtrate with stirring, the mixture allowed to stand overnight and then filtered. The solid which was collected was washed with saturated brine (350 ml), and dried, and extracted with boiling absolute ethanol. The extract was filtered, the ethanol evaporated and the residue stirred with ether (500 ml) for 2 hours. The mixture was filtered leaving sodium 6-bromo-2-naphthol-1-sulphonate. A portion (6.3 g) of this was dissolved in water (250 ml) filtered and cooled. This was then added slowly to a diazonium salt, obtained by slowly adding ice-cold aqueous sodium nitrite (1.7 g. in 5 ml. water) to a cooled solution of m-trifluoromethylaniline (3.22 g.) in concentrated hydrochloric acid (8 ml.) and water (30 ml.). A yellow precipitate formed which was filtered off, washed with cold saturated brine (250 ml.) and made into a paste with cold water (100 ml.) The paste was cooled to 0° C. and sodium carbonate (6 g.) added with stirring. After 1½ mins. cold aqueous sodium hydroxide (12 g. in 30 ml. water) was added and after a red solution had formed, the mixture was stirred on an ice-bath for 3 hours and then at room temperature overnight. The mixture was acidified to pH 2-3 with concentrated hydrochloric acid and then brought to pH 8 with saturated aqueous sodium carbonate. The mixture was filtered and the filtrate acidified to pH 1 with concentrated hydrochloride acid, whilst stirring. The solid was filtered off and dissolved in warm water (150 ml.) and the solution refluxed for two hours during which time concentrated hydrochloric acid (15 ml.) was added. The mixture was then cooled, the solid filtered off and recrystallised from a 2:1 mixture of acetic acid and water to give 7-bromo-4-hydroxy-2-(3-trifluoromethylphenyl)-DPA mp 217°-219° C.

EXAMPLES 102-136

In a similar manner to that described in Example 101 there was obtained from the appropriate 2-naphthol and aniline, the corresponding acetic acid. The compounds obtained are set out in Table 1. In some cases the diluted reaction mixture from the sulphonation of the 2-naphthol or a solution of the crude sodium naphthol sulphonate was reacted with the diazonium salt solution without purification. In some case also, neutral and phenolic impurities from the final acetic acid were removed by partition between a water immiscible solvent, usually ether, and aqueous sodium hydrogen carbonate. The product was then recovered from the aqueous phase by acidification.

TABLE 1

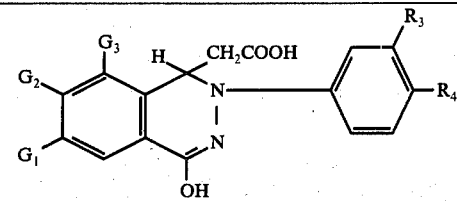

| Ex. No. | Aniline | 2-naphthol | R₃ | R₄ | G₁ | G₂ | G₃ | m.p. (° C) |
|---|---|---|---|---|---|---|---|---|
| 102 | 3-methylthio | 6-bromo | MeS | H | H | Br | H | 232-233 |
| 103 | 3-nitro | 6-bromo | NO₂ | H | H | Br | H | 228-230 |
| 104 | 3-chloro | 6-bromo | Cl | H | H | Br | H | 166-168 |
| 105 | 3-nitro | 6-methoxy | NO₂ | H | H | MeO | H | 217-218 |
| 106 | 3-methylthio | 6-methoxy | MeS | H | H | MeO | H | 233-235 |
| 107 | 3-nitro | 6-t-butyl | NO₂ | H | H | Buᵗ | H | 244-245 |
| 108 | 3-trifluoromethyl | 6-ethyl | CF₃ | H | H | Et | H | 202-206 |
| 109 | 3-nitro | 6-ethyl | NO₂ | H | H | Et | H | 220-222 |
| 110 | 3-methylthio | 6-ethyl | MeS | H | H | Et | H | 195-196 |
| 111 | 3-trifluoromethyl | 6-methyl | CF₃ | H | H | Me | H | 219 |
| 112 | 3-nitro | 6-methyl | NO₂ | H | H | Me | H | 233-233.5 |
| 113 | 3-chloro | 6-methyl | Cl | H | H | Me | H | 210-211 |

TABLE 1-continued

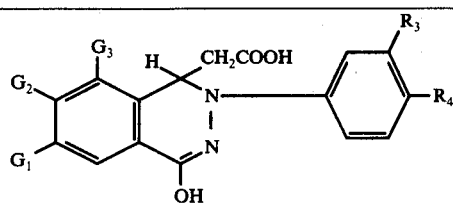

| Ex. No. | Aniline | 2-naphthol | R₃ | R₄ | G₁ | G₂ | G₃ | m.p. (° C) |
|---|---|---|---|---|---|---|---|---|
| 114 | 4-chloro | 6-methyl | H | Cl | H | Me | H | 215–216 |
| 115 | 3-methylthio | 6-methyl | MeS | H | H | Me | H | 208–209 |
| 116 | 3-bromo | 6-methyl | Br | H | H | Me | H | 231–232 |
| 117 | 3-nitro | 6-chloro | NO₂ | H | H | Cl | H | 227–229 |
| 118 | 3-methylthio | 6-chloro | MeS | H | H | Cl | H | 218 |
| 119 | 3-nitro | 6-fluoro | NO₂ | H | H | F | H | 242–243 |
| 120 | 3-nitro | 7-fluoro | NO₂ | H | F | H | H | 232–235 |
| 121 | 3-nitro | 6,7-dichloro | NO₂ | H | Cl | Cl | H | 234–235 |
| 122 | 3-chloro | 6-ethyl | Cl | H | H | Et | H | 215–220 |
| 123 | 3-trifluoromethyl | 6-chloro | CF₃ | H | H | Cl | H | 197–198 |
| 124 | 3-nitro | 6-isopropyl | NO₂ | H | H | Pr$^i$ | H | 226–227 |
| 125 | 3-trifluoromethyl | 6-fluoro | CF₃ | H | H | F | H | 123–124 |
| 126 | 3-trifluoromethyl | 7-fluoro | CF₃ | H | F | H | H | 228–229 |
| 127 | 4-methylthio | 6-methyl | H | MeS | H | Me | H | 182–186 |
| 128 | 3-nitro | 5-chloro | NO₂ | H | H | H | Cl | 230–231 |
| 129 | 3-nitro | 5,6-dimethyl | NO₂ | H | H | Me | Me | 268–270 |
| 130 | 3-nitro | 7-ethyl | NO₂ | H | Et | H | H | 138–140 |
| 131 | 3-nitro | 5-fluoro | NO₂ | H | H | H | F | 211–213 |
| 132 | 3-fluoro | 6-methyl | F | H | H | Me | H | 207–209 |
| 133 | 3-iodo | 6-methyl | I | H | H | Me | H | 228–230 |
| 134 | 3-acetyl | 6-methyl | CH₃CO | H | H | Me | H | 195–196 |
| 135 | 3-nitro | 6-methylthio | NO₂ | H | H | MeS | H | 238 |
| 136 | 4-methyl-3-nitro | 6-methyl | NO₂ | Me | H | Me | H | 138–140 |
| 137 | 3-trifluoroacetyl | 6-chloro | CF₃CO | H | H | H | Cl | 130–140 |

EXAMPLES 138–147

In a similar manner as described in Example 1 starting from 1,2,3-benzothiadiazol-5-ylamine and the appropriate naphthol, the acid set out in Table II were obtained.

TABLE II

| Ex. No. | 2-Naphthol | G₁ | G₂ | G₃ | m.p. (° C) |
|---|---|---|---|---|---|
| 138 | 6-methyl | H | Me | H | 234 |
| 139 | 6-chloro | H | Cl | H | *233 |
| 140 | 6-fluoro | H | F | H | 254–255 |
| 141 | 7-fluoro | F | H | H | 274–275 |
| 142 | 6-isopropyl | H | Pr$^i$ | H | 230–231 |
| 143 | 5,6-dimethyl | H | Me | Me | 210–212 |
| 144 | 6-t-butyl | H | Bu$^t$ | H | 232–234 |
| 145 | 6-ethyl | H | Et | H | 235 |
| 146 | 7-chloro | Cl | H | H | 265 |
| 147 | 6-benzoyl | H | PhCO | H | 164–166 |

*This product is obtained in two forms, having different infra-red spectra. Recrystallisation from acetic acid gives a product having $v_{max}$ 1710, 1680 cm⁻¹, whereas recrystallisation from ethyl acetate gives a product having $v_{max}$ 1700, 1635 cm⁻¹ (KBr disc).

The product is obtained in two forms, having different infra-red spectra. Recrystallisation from acetic acid gives a product having $v_{max}$ 1710, 1680 cm⁻¹, whereas recrystallisation from ethyl acetate gives a product having $v_{max}$ 1700, 1635 cm⁻¹ (KBr disc).

EXAMPLES 148–150

The product of Example 112 (2.8 g) was dissolved in aqueous potassium hydroxide (6.3 g in 63 3.2 of water). Dimethyl sulphate (3.2g) was added and the mixture stirred at room temperature for ½ hour. The solution was cooled to 0° C and acidified with concentrated hydrochloric acid. The yellow precipitate, which formed, was filtered off and recrystallised from a mixture of acetic acid and water (2:1) to give 3,7-dimethyl-2-(3-nitrophenyl)-4-oxo-TPA, m.p. 217°–219° C. (Example 148).

In a similar manner, the product of Example 139 gave 2-(1,2,3-benzothiadiazol-5-yl)-7-chloro-3-methyl-4-oxo TPA, m.p. 260°–261° C. (Example 149) and the product of Example 136 gave 3,7-dimethyl-2-(4-methyl-3-nitrophenyl)-4-oxo-TPA, m.p. 201°–202° C (Example 150).

EXAMPLES 151–156

The product of Example 148 (19 g) was esterified by refluxing with methanol (700 ml) containing concentrated sulphuric acid (15 ml) for 6 hours. The mixture was evaporated to 150 ml. cooled and poured into icewater. The solid was collected, washed with saturated aqueous sodium hydrogen carbonate, followed by water, dried and recrystallised from methanol to give methyl 3,7-dimethyl-2-(3-nitrophenyl)-4-oxo-TPAE, m.p. 179°–180° C (Example 151).

In a similar manner the product of Example 138 gave methyl 2-(1,2,3-benzothiadiazol-5-yl)-4-hydroxy-7-methyl-DPAE, m.p. 202°–203° C (Example 152); the product of Example 139 gave methyl 2-(1,2,3-benzothiadiazol-5-yl)-7-chloro-4-hydroxy-DPAE, m.p. 220°–222° C (Example 153); the product of Example 150 gave methyl 3,7-dimethyl-2-(4-methyl-3-nitro phenyl)-4-oxo-TPAE, m.p. 177°–178° C (Example 154); the product of Example 171 gave methyl 2-(1,2-benzoisothiazol-5-yl)-4-hydroxy-7-methyl-DPAE, m.p. 120°–127° C. (Example 155) and the product of Example 136 gave methyl 4-hydroxy-7-methyl-2-(4methyl-3-nitrophenyl)-DPAE, m.p. 188°–189° C (Example 156).

EXAMPLE 157

The product of Example 148 (1.4 g) was dissolved in IMS (200 ml), mixed with palladium-charcoal (10% Pd;

0.5 g) and formaldehyde (40%; 1.0 ml) and the mixture hydrogenated with hydrogen (440 ml) with shaking. The mixture was filtered, evaporated under reduced pressure and the residue allowed to stand to 0° C. White crystals, which formed, were filtered off, washed with and recrystallised from IMS and dried in vacuo to give 2-(3-N,N-dimethylaminophenyl)-3,7-dimethyl-4-oxo-TPA, m.p. 202°–204° C.

EXAMPLES 158–160

The product of Example 151 (14 g) was dissolved as in methanol (1 liter) and hydrogenated at room temperature using a palladium-charcoal catalyst (10%; 1 g). The mixture was filtered and the filtrate concentrated to give crystals of methyl 2-(3-aminophenyl)-3,7-dimethyl-4-oxo-TPAE, m.p. 184°–185° C (Example 158).

In a similar manner the product of Example 112 gave 2-(3-aminophenyl)-4-hydroxy-7-methyl-DPA, m.p. 191° C (Example 159) and the product of Example 148 gave 2-(3-aminophenyl)-3,7-dimethyl-4-oxo-TPA, m.p. 216°–217° C (Example 160).

EXAMPLE 161

A solution of p-toluene sulphonyl chloride (3.1 g.) in pyridine (11 ml.) was added to a solution of the product of Example 158 (5.6 g.) in pyridine (33 ml.). The mixture was refluxed for 1 hour, cooled and poured onto ice-water. The aqueous layer was removed and the remaining gum stirred with light petroleum (b.p. 80°–100° C). The solid product was filtered and recrystallised from IMS to give methyl 3,7-dimethyl-4-oxo-2-(3-p-toluenesulphon amidophenyl)-TPAE, m.p. 205°–206° C. This was mixed with sodium carbonate (3.65 g.), dimethyl sulphate (2.5 ml.) and acetone and the mixture stirred and refluxed for 2 hours. The acetone was evaporated and the residue treated with a mixture of ethyl acetate and water. The organic layer was washed with water, dried and evaporated and the product recrystallised from IMS to give methyl 3,7-dimethyl-2-(3-N-methylp-toluenesulphonamidophenyl)-4-oxo-TPAE, m.p. 172°–173° C. This was dissolved in IMS and hydrolysed by treatment with aqueous sodium hydroxide, followed by evaporation. The residue was dissolved in water, filtered and acidified and the product filtered, washed with water and recrystallised from aqueous acetic acid to give 3,7-dimethyl-2-(3-N-methyl-p-toluenesulphonamidophenyl)-4-oxo-TPA, m.p. 214°–215° C.

EXAMPLE 162

The product of Example 158 (11 g.) was refluxed with glacial acetic acid (100 ml.) for 18 hours. The mixture was then evaporated to give an oil which was triturated with methanol. The solid product was recrystallised from methanol to give methyl 2-(3-acetamidophenyl)-3,7-dimethyl-4-oxo-TPAE, m.p. 224°–225° C. 3g. of this was dissolved in dioxan (75 ml.), sodium hydride (0.6g.) added and the mixture refluxed for 2 hours. It was then cooled and dimethylsulphate (1.2 ml.) added and refluxed for a further 4 hours. The mixture was evaporated and the remaining gum washed with water and extracted with dichloromethane. The extract was washed with aqueous sodium hydrogen carbonate and water, dried, evaporated and the residue recrystallised from ethyl acetate to give methyl 3,7-dimethyl-2-[3-(N-methylacetamido)phenyl]-4-oxo-TPAE, m.p. 190° C.

EXAMPLE 163

The product of Example 162 was hydrolysed in a similar manner to that described in Example 161 to give 3,7-dimethyl-2-[3-(N-methylacetamido)phenyl]-4-oxo-TPA, m.p. 228°–230° C.

EXAMPLE 164

To a cooled solution of the product of Example 148 (5g.) in dry tetrahydrofuran (25 ml.) and triethylamine (2 ml.) was added, dropwise, a solution of methyl chloroformate (1.1 ml.) in dry tetrahydrofuran (5 ml.). The mixture was stirred at −5° C for 30 mins and then filtered. The filtrate was added dropwise with stirring to a solution of sodium borohydride (1.6 g.) in water. The mixture was stirred for 3 hours and then acidified with hydrochloric acid (2N:50 ml.). The solid was extracted with dichloromethane and the extract washed with aqueous sodium hydrogen carbonate, dried and evaporated to give a gum which was triturated with ether. The solid, which separated, was recrystallised from methanol to give 3,7-dimethyl-1-(2-hydroxyethyl)-2-(3-nitrophenyl)-4-oxo-1,2,3,4-tetrahydrophthalazine, m.p. 169°–170° C.

EXAMPLE 165

The product of Example 158 (3g.) was diazotised using sodium nitrite and hydrochloric acid. Aqueous fluoroboric acid (42%;24 ml.) was added and the yellow precipitate of the diazonium fluorobate was filtered, washed with an ether/methanol mixture (4:1) and then mixed with methanol (50 ml.). The mixture was heated to 50° C. Nitrogen was evolved and the solid dissolved. The red solution was poured into water (200 ml.) and the solid which separated was extracted with chloroform. The extract was dried and evaporated and the residue recrystallised from methanol to give methyl 2(3-methoxyphenyl)-3,7-dimethyl-4-oxo-TPAE, m.p. 120°–121° C.

EXAMPLE 166

The product of Example 158 (1g.) was diazotised and treated with fluoroboric acid as described in Example 65 to give the diazonium fluorobate which was filtered, washed with aqueous ice-cold fluoroboric acid (10%, 5ml.), ice-cold methanol (10 ml.), an ice-cold methanol/ether mixture (1:1; 10 ml.) and ice-cold ether (10 ml.). The solid was dried in vacuo and then added to an ice-cold solution of potassium carbonate (205 mg.) in trifluoroacetic acid (6.3 ml.). The mixture was refluxed for 45 mins, cooled and poured into water (30 ml.). The solid was dissolved in dichloromethane and the solution extracted with aqueous sodium hydroxide (2N;30 ml.). The extract was treated with charcoal, filtered and the filtrate acidified with hydrochloric acid (5N). The precipitate was filtered, dried in vacuo and recrystallised from a mixture of ethylacetate and light petroleum (b.p. 60°–80° C) to give 2-(3-hydroxyphenyl)-3,7-dimethyl-4-oxo-TPA, m.p. 150°–152° C.

EXAMPLE 167

In a similar manner to that described in Example 48 but replacing the dimethyl sulphate with diethyl sulphate, the product of Example 112 gave 3-ethyl-7-methyl-2-(3-nitrophenyl)-4-oxo-TPA, m.p. 232°–233° C.

EXAMPLE 168

The product of Example 112 (1 g.) was mixed with acetic anhydride (5 ml.) and the mixture heated on a steam bath for 1 hour. Excess acetic anhydride was evaporated under reduced pressure and the residue triturated with light petroleum (b.p. 40°-60° C) to give a yellow solid which was recrystallised from a mixture of ether and light petroleum (b.p. 40°-60° C) to give 4-acetoxy-7-methyl-2-(3-nitrophenyl)-DPA, m.p. 204°-205° C.

EXAMPLE 169

The product of Example 151 (1.5 g.) dissolved in xylene (65 ml.) was mixed with phosphorous pentasulphide (0.81 g.) and the mixture boiled under reflux for 1 hour and filtered. The filtrate was evaporated under reduced pressure and the residue recrystallised from light petroleum (b.p. 80°-100° C) to give methyl 3,7-dimethyl-2-(3-nitrophenyl)-4-thioxo-TPAE, m.p. 160°-161° C.

EXAMPLE 170

The product of Example 159 (5g.) was diazotised using sodium nitrite and hydrochloric acid. Mercuric bromide (2.3g.) was added and the red precipitate collected, washed with ice-cold water and acetone, dried and added to hexamethylphosphoric triamide (40 ml.). The mixture was heated at 40° C until gas evolution ceased, cooled, poured into water and the solid produced, collected, washed with water and recrystallised from aqueous IMS to give 4-hydroxy-7-methyl-2-phenyl-DPA, m.p. 223°-224° C.

EXAMPLE 171-174

In a similar manner as described in Example 100 starting from the appropriate naphthol and aromatic amine, the acids set out in Table III were obtained.

EXAMPLE 175

The product of Example 115 (2 g) was dissolved in glacial acetic acid and aqueous hydrogen peroxide (1.4 ml of 100 vol diluted to 5 ml) added. The mixture was stirred at 30° C for 30 minutes, then concentrated by evaporation and diluted with water, filtered and the filtrate allowed to stand to give 4-hydroxy-7-methyl-2-(3-methylsulphinylphenyl)-DPA, m.p. 188°-191° C.

EXAMPLE 176

In a similar manner as Example 175 the product of Example 35 gave 4-hydroxy-7-methylsulphinyl-2-(3-nitrophenyl)-DPA, m.p. 150°-153° C.

EXAMPLE 177

The product of Example 139 (100 mg) was added to saturated aqueous sodium hydrogen carbonate (100 ml) and the mixture evaporated to reduced volume. The solid, which crystallised, was recrystallised from ethanol to give sodium 2-(1,2,3-benzothiadiazol-5-yl) -7-chloro-4-hydroxy-DPAE, m.p. above 300° C.

EXAMPLE 178

Phosphorus pentasulphide (4 g) was added portionwise to a stirred solution of methyl 3-methyl-2-(3-nitrophenyl)-4-oxo-TPAE (3.2 g) in boiling xylene. After heating under reflux for 2½ hours the hot solution was filtered. The filtrate was evaporated under reduced pressure and the residue triturated with ether to give a bright yellow solid. Recrystallisation from light petroleum (b.p. 120° C) gave methyl 3-methyl-2-(3-nitrophenyl)-4-thioxo-TPAE, m.p. 147.5°-148° C.

The ester (1.11g) was then hydrolysed by suspending in a boiling mixture of ethanol (20 ml) and aqueous sodium hydroxide (2.5N, 2.4 ml). After 1 hour under reflux the solution was acidified with aqueous hydrochloric acid (2N, 3ml), cooled and diluted with water. The mixture was extracted with chloroform. The chlo-

TABLE III

[Structure shown with G₂ substituent on benzene ring fused to ring bearing H, CH₂COOH, N—Ar, =N, OH substituents]

| Ex. No. | Amine | 2-naphthol | Ar | G₂ | m.p. (° C) |
|---|---|---|---|---|---|
| 171 | 1,2-benzoisothiazol-5-ylamine | 6-methyl | 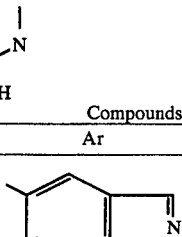 | Me | 150–200 |
| 172 | 1,2-benzoisothiazol-5-ylamine | 6-chloro | 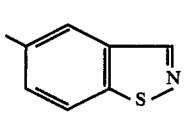 | Cl | 165–170 |
| 173 | benzothiazol-5-ylamine | 6-ethyl | 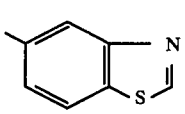 | Et | 229–231 |
| 174 | benzothiazol-5-ylamine | 6-methyl | 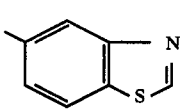 | Me | 251–253 | roform extracts were washed with water, dried with anhydrous magnesium sulphate and evaporated to give a residue which solidified on trituration with ether. Recrystallisation of the solid from ethyl acetate — light petroleum (b.p. 62°–68° C) gave orange-yellow crystals of 3-methyl-2-(3-nitrophenyl)-4-thioxo-TPA, m.p. 199°–201° C.

EXAMPLE 179

In a similar manner to that described in Example 178 the product of Example 90 was converted into methyl 3-methyl-4-thioxo-2-(3-trifluorophenyl)-TPAE, m.p. 140°–141° C, which was hydrolysed to 3-methyl-4-thixo-2-(3-trifluormethylphenyl)-TPA, m.p. 197°–198° C.

EXAMPLE 180

In a similar manner to that described in Example 1, starting from 5-amino-6-bromindan, there was obtained 2-(6-bromoindan-5-yl)-4-hydroxy-DPA, m.p. 247°–249° C. This was hydrogenated with hydrogen in the presence of palladised charcoal, acetic acid and aqueous sodium acetate at 50° C to give 4-hydroxy-2-(indan-5-yl)-1,2-DPA, m.p. 235° C.

EXAMPLE 181

In a similar manner to that described in Example 180 but starting from 3-bromo-4,4-dimethoxyaniline there was obtained 2-(3-bromo-4,5-dimethoxyphenyl)-4-hydroxy-DPA, m.p. 100°–102° C which on hydrogenation gave 2-(4,5-dimethoxyphenyl)-4-hydroxy-DPA, m.p. 216°–217° C.

EXAMPLE 182

In a similar manner to that described in Example 66, the product of Example 63 was hydrolysed to give 3-methyl-2-(3-N-methylmethanesulphonamidophenyl)-TPA, m.p. 203°–204° C.

EXAMPLE 183

In a similar manner to that described in Example 74, the product of Example 19 was methylated to give 3-methyl-2-(3-methylthiophenyl)-4-oxo-TPA, m.p. 178°–179° C.

EXAMPLE 184

The product of Example 1 was dissolved in an equivalent amount of aqueous sodium hydroxide. The solution was evaporated to dryness and recrystallised from a mixture of absolute alcohol and ether to give sodium 4-hydroxy-2-(3-trilfuoromethylphenyl)-DPAE which decomposed on heating above 250° C.

EXAMPLE 185

The product of Example 1 (1.0g) was mixed with thionyl chloride (4 ml) and allowed to stand at room temperature overnight. Dry, light petroleum (b.p. 60°–80° C) was added, whereupon an orange solid formed which was collected, washed with light petroleum and dried in vacuo. 1 gram of this product was added portionwise to a cooled suspension of lithium aluminium tri-t-butoxy hydride prepared from lithium aluminium hydride (0.44 g) and t-butanol (2.6 g) in diglyme (5 ml). The mixture was stirred overnight, cooled with ice and then decomposed with sulphuric acid (5N). The solid filtered, washed with dichloromethane which was combined with dichloromethane extracts of the filtrate. The extracts were washed with aqueous sodium bicarbonate, dried and evaporated under reduced pressure. The residue was recrystallised from a mixture of light petroleum and ethyl acetate to give 4-hydroxyl-1-(2-hydroxyethyl)-2-(3-trifluoromethylphenyl)-1,2-dihydrophthalazine, m.p. 183°–185° C.

EXAMPLE 186

The product of Example 1 was dissolved in dry tetrahydrofuran and mixed with an equivalent amount of triethylamine. The mixture was evaporated to dryness and the residue triturated with ether. The solid was recrystallised from a mixture of isopropanol and ether to give triethylammonium 4-hydroxy-2-(3-trifluoromethylphenyl)-DPAE, m.p. 148°–149° C.

EXAMPLE 187

The product of Example 9 was esterified with ethanol in a similar manner to that described in Example 60 to give ethyl 4-hydroxy-2-(3-iodophenyl)-DPAE, m.p. 174°–175° C.

EXAMPLE 188

The product of Example 187 (2 g.) was mixed with cuprous cyanide (0.6g.) and dimethyl formamide (25 ml.) and the mixture refluxed for 6 hours, cooled and poured into water. The solid which formed was collected, washed with dilute hydrochloric acid and water and extracted with dichloroethane. The extracts were evaporated to dryness and the solid recrystallised from ethyl acetate to give ethyl 2-(3-cyanophenyl)-4-hydroxy-DPAE, m.p. 213°–214° C.

EXAMPLE 189

In a similar manner to that described in Example 180 there was obtained 2-(2,4-dibromo-5-t-butylphenyl)-4-hydroxy-DPA, m.p. 241° C. which was debrominated to give 2-(3-t-butylphenyl)-4-hydroxy-DPA, m.p. 161°–163° C.

EXAMPLE 190

In a similar manner to that described in Example 74, the product of Example 41 was methylated to give 2-(4-chloro-3-nitrophenyl)-3-methyl-4-oxo-TPA, m.p. 206°–208° C.

EXAMPLE 191

In a similar manner to that described in Example 95 the intermediate A from Example 1, was treated up to and including the addition of the reaction mixture to aqueous acetic acid. The solution obtained was extracted with dichloromethane and the extracts washed with aqueous sodium bicarbonate, dried and evaporated under reduced pressure to give 4-hydroxy-1-(2-hydroxyethyl)-2-(3-trifluoromethyl phenyl)-1,2-dihydrophthalazine, m.p. 183°–184° C.

EXAMPLE 192

The product of Example 175 was oxidised with further hydrogen peroxide at 100° C. to give 4-hydroxy-7-methyl-2-(3-methylsulphonylphenyl)-DPA, m.p. 139°–145° C.

EXAMPLE 193

In a similar manner to that described in Example 151 the product of Example 115 gave methyl 4-hydroxy-7-methyl-2-(3-methylthiophenyl)-DPAE, m.p. 148.5°–149° C.

EXAMPLE 194–197

In a similar manner as described in Example 1, starting from 1,2,3-benzothiadiazol-5-ylamine and the appropriate naphthol, the acids set out in Table IV were obtained.

TABLE IV

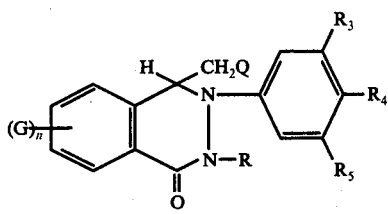

| Ex. No. | 2-Naphthol | Compounds obtained G$_2$ | m.p. (° C.) |
|---|---|---|---|
| 194 | 6-n-propyl | Pr$^n$ | 237–238 |
| 195 | 6-bromo | Br | 195–198 |
| 196 | 6-methoxy | Meo | 212 |
| 197 | 6-methylthio | MeS | 188–190 |

EXAMPLE 198

In a similar manner to that described in Example 167 the product of Example 139 gave 2-(1,2,3-benzothiazol-5-yl)-7-chloro-3-ethyl-4-oxo-TPA, m.p. 235°–236° C.

EXAMPLE 199

The following mixture is formed into tablets in conventional manner, each tablet containing 2 mg. of active ingredient.

|  | Parts |
|---|---|
| 4-Hydroxy-7-methyl-2-(3-methylthiophenyl)-1,2-dihydrophthalazine-1-acetic acid | 50 |
| maize starch | 30 |
| lactose | 163 |
| stearic acid | 1 |

Compositions similar to that described above are prepared containing as active ingredient the final products of Examples 1–114 and 116–199 as well as the following compounds:
4-hydroxy-2-(3-nitrophenyl)-DPA;
2-(3-chlorophenyl)-4-hydroxy-DPA;
4-hydroxy-2-phenyl-DPA;
3-methyl-2-(3-nitrophenyl)-4-oxo-TPS;
4-acetoxy-2-(3-nitrophenyl)-DPA;
and the methyl and ethyl esters of 4-hydroxy-2-(3-nitrophenyl)-DPA.

The substituted 2-naphthol-1-sulphonic acids and their sodium salts which are intermediates in Examples 101–147 are novel compounds.

We claim:

1. A therapeutic composition for inducing diuresis in mammals comprising a therapeutically effective diuretic amount of a compound of the formula:

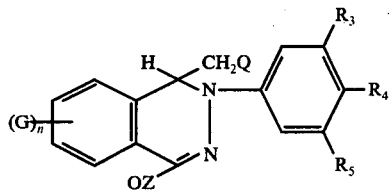

or its enol form of the formula:

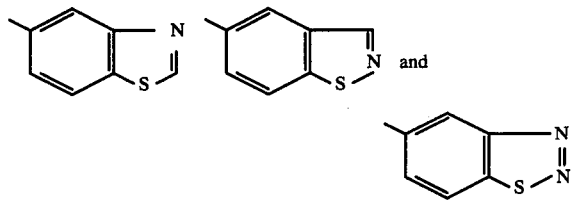

wherein Q is selected from the group consisting of COOH and CH$_2$OH, R is selected from the group consisting of hydrogen and C$_{1-7}$ alkyl, Z is hydrogen or acetyl, R$_5$ is hydrogen, R$_3$ and R$_4$ are each independently selected from the group consisting of hydrogen, fluorine, chlorine, bromine, iodine, nitro, cyano, C$_{1-7}$ alkyl, trifluoromethyl, 1-hydroxypropyl, methoxymethyl, phenyl, C$_{1-4}$ alkoxy, C$_{1-4}$ alkylthio, trifluorometylthio, phenylthio, methylsulphonyl, methylsulphinyl, acetyl, propionyl, trifluoroacetyl, benzoyl, thenoyl, hydroxy, sulphamoyl, N,N-dimethylsulphamoyl, N,N-diethylsulphamoyl, amino, N-methylamino, N,N-dimethylamino, N-ethylamino, N,N-diethylamino, N,N-methylethylamino, N-methylformamido, N-methylacetamido, N-methylmethanesulphonamido, N-methyl-p-toluenesulphonamido, 1-pyrrolyl, or R$_3$ and R$_4$ together form a portion of a heterocyclic ring fused to the benzene ring to form a group selected from the group consisting of:

wherein n is 0 or 1 and G is in the 7-position and is selected from the group consisting of fluorine, chlorine, bromine, C$_{1-4}$ alkyl, C$_{1-4}$ alkylthio and C$_{1-4}$ alkoxy or is in the 6 position and is fluorine, or a pharmaceutically acceptable alkyl having 1 to 7 carbon atoms inclusive ester or salt of those compounds in which Q is COOH; said compound being in admixture with a pharmaceutically acceptable carrier.

2. A therapeutic composition according to claim 1 wherein R$_5$ is hydrogen, n is 1 and G is in the 7-position, Q is carboxy, X is oxygen, R$_4$ is hydrogen and R$_3$ is other than hydrogen or R$_3$ and R$_4$ together form a portion of a heterocyclic ring fused to the benzene ring, as well as salts thereof.

3. A therapeutic composition according to claim 2 wherein G is chlorine, fluorine, methyl, ethyl, isopropyl or methoxy and when R (or Z) is hydrogen, R$_3$ is nitro, trifluoromethyl, methylthio, chloro or bromo or R$_3$ and R$_4$ together with the benzene ring to which they are attached are benzothiazol-5-yl, 1,2,3-benzothiadiazol-5-yl or 1,2-benzoisothiazol-5-yl and when R is methyl, R$_3$ is N,N-dimethylamino.

4. A therapeutic composition of claim 1 wherein the active diuretic ingredient is 2-(1,2,3-benzothiadiazol-5-yl)-7-chloro-4-hydroxy-1,2-dihydrophthalazine-1acetic acid.

5. A therapeutic composition of claim 1 wherein the active diuretic ingredient is 2-(1,2,3-benzothiadiazol-5- yl)-7-ethyl-4-hydroxy-1,2-dihydrophthalazine-1-acetic acid.

6. A therapeutic composition of claim 1 wherein the active diuretic ingredient is 2-(1,2,3-benzothiazol-5-yl)-7-chloro-3-methyl-4-oxo-1,2,3,4-tetrahydrophthalazine-1-acetic acid.

7. A therapeutic composition of claim 1 wherein the active diuretic ingredient is 4-hydroxy-7-methyl-2-(3-trifluoromethylphenyl)-1,2-dihydrophthalazine-1-acetic acid.

8. A therapeutic composition of claim 1 wherein the active diuretic ingredient is 4-hydroxy-7-methyl-2-(3-methylthiophenyl)-1,2-dihydrophthalazine-1-acetic acid.

9. A therapeutic composition according to claim 1 suitable for oral administration and in the form of tablets, capsules, lozenges, powders, effervescent granules, syrups or aqueous or oily suspensions.

10. A therapeutic composition according to claim 1 suitable for rectal administration and in the form of a suppository.

11. A therapeutic composition according to claim 1 comprising 0.1 to 90% by weight of the compound.

12. A therapeutic composition according to claim 1 in unit dose form comprising 0.1 mg. to 500 mg. of the compound.

13. A method of inducing diuresis and saluresis in mammals which compromises administering to the mammal a pharmaceutically acceptable and effective amount of a compound disclosed in claim 1.

14. A method according to claim 13 which comprises administering 0.1 mg–2 g. of compound per subject per day.

15. A method according to claim 14 which comprises administering 3 mg–2 g. of compound per subject per day.

16. A compound of the formula:

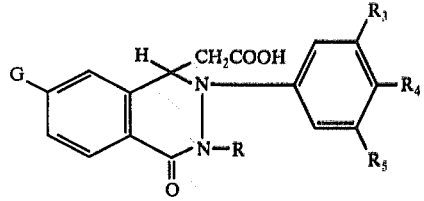

or its enol form having the formula:

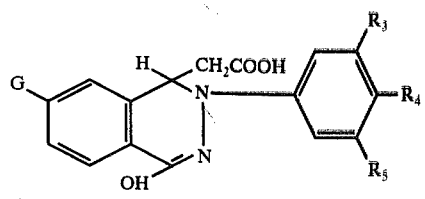

wherein, R is selected from the group consisting of hydrogen and $C_{1-7}$ alkyl, $R_5$ is hydrogen, $R_3$ and $R_4$ together with the benzene to which they are attached form a fused ring system selected from the group consisting of:

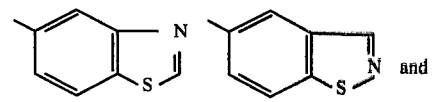 and

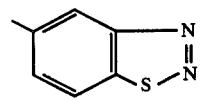

and wherein G is selected from the group consisting of fluorine, chlorine, bromine, $C_{1-4}$ alkyl and $C_{1-4}$ alkoxy, and pharmaceutically acceptable salts and alkyl having 1 to 7 carbon atoms inclusive esters of these compounds.

17. A compound according to claim 16 in which G is selected from the group consisting of methyl, ethyl, isopropyl, methoxy, fluorine, chlorine and bromine.

18. The compound of claim 16 which is 2-(1,2,3-benzothiadiazol-5-yl)-7-ethyl-4-hydroxy-1,2-dihydrophthalazine-1-acetic acid.

19. The compound of claim 16 which is 2-(1,2,3-benzothiadiazol-5-yl)-7-chloro-3-methyl-4-oxo-1,2,3,4-tetrahydrophthalazine-1-acetic acid.

20. The compound of claim 16 which is 2-(1,2,3-benzothiadiazol-5-yl)-4-hydroxy-7-methyl-1,2-dihydrophthalazine-1-acetic acid.

21. The compound of claim 16 which is 2-(1,2,3-benzothiadiazol-5-yl)-4-hydroxy-7-bromo-1,2-dihydrophthalazine-1-acetic acid.

22. The compound of claim 16 which is 2-(1,2,3-benzothiadiazol-5-yl)-7chloro-4-hydroxy-1,2-dihydrophthalazine-1-acetic acid.

23. A compound of the formula:

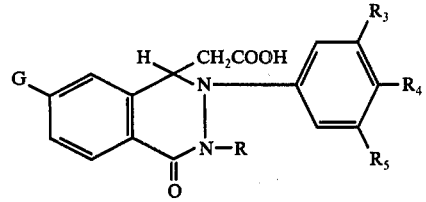

or its enol form having the formula:

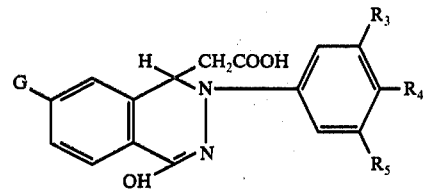

wherein R is selected from the group consisting of hydrogen and $C_{1-7}$ alkyl $R_4$ and $R_5$ are hydrogen, $R_3$ is selected from the group consisting of trifluoromethyl, trifluoroacetyl, N,N-dimethylamino and methylthio and wherein G is selected from the group consisting of fluorine, chlorine, bromine, $C_{1-4}$ alkyl and $C_{1-4}$ alkoxy, and pharmaceutically acceptable salts and alkyl having 1 to 7 carbon atoms inclusive esters of these compounds.

24. A compound according to claim 23 in which G is selected from the group consisting of methyl, ethyl, isopropyl, methoxy, fluorine, chlorine and bromine.

25. The compound of claim 23 which 4-hydroxy-7-methyl-2-(3-methylthiophenyl)-1,2-dihydrophthalazine-1-acetic acid.

26. The compound of claim 23 which is 2-(3-N,N-dimethylaminophenyl)-3-methyl-4-oxo-1,2,3-tetrahydrophthalazine-1-acetic acid.

27. The compound of claim 23 which is 4-hydroxy-7-methyl-2-(3-trifluoromethylphenyl)-1,2-dihydrophthalazine-1-acetic acid.

28. The compound of claim 23 which is 4-hydroxy-7-chloro-2-(3-trifluoroacetylphenyl)-1,2-dihydrophthalazine-1-acetic acid.

29. The compound of claim 23 which is 4-hydroxy-7-methoxy-2-(3-methylthiophenyl)1,2-dihydrophthalazine-1-acetic acid.

* * * * *